US008101417B2

(12) United States Patent  (10) Patent No.: US 8,101,417 B2
Conway et al.  (45) Date of Patent: Jan. 24, 2012

(54) CARBON MEASUREMENT IN AQUEOUS SAMPLES USING OXIDATION AT ELEVATED TEMPERATURES AND PRESSURES

(75) Inventors: Gregory B. Conway, Longmont, CO (US); Michael R. Scaer, Louisville, CO (US); Paul Melanson, Boulder, CO (US); Gordon K. Francis, Louisville, CO (US); Pei Huang, Lafayette, CO (US)

(73) Assignee: GE Analytical Instruments, Boulder, CO (US)

( * ) Notice: Subject to any disclaimer, the term of this patent is extended or adjusted under 35 U.S.C. 154(b) by 0 days.

(21) Appl. No.: 12/733,276

(22) PCT Filed: Aug. 29, 2008

(86) PCT No.: PCT/US2008/010265
§ 371 (c)(1),
(2), (4) Date: Feb. 22, 2010

(87) PCT Pub. No.: WO2009/032205
PCT Pub. Date: Mar. 12, 2009

(65) Prior Publication Data
US 2010/0159602 A1  Jun. 24, 2010

Related U.S. Application Data

(60) Provisional application No. 60/967,576, filed on Sep. 5, 2007.

(51) Int. Cl.
*G01N 35/00* (2006.01)
*G01N 33/00* (2006.01)
*B01J 19/00* (2006.01)
*B01J 8/00* (2006.01)

(52) U.S. Cl. ........................................ 436/146; 436/145
(58) Field of Classification Search .................... 436/25, 436/146, 145; 73/152.28, 152.23, 152.01
See application file for complete search history.

(56) References Cited

U.S. PATENT DOCUMENTS

| | | | |
|---|---|---|---|
| 3,296,435 A | 1/1967 | Teal et al. | |
| 3,700,891 A | 10/1972 | Luft | |
| 3,958,945 A | 5/1976 | Takahashi | |
| 4,294,799 A * | 10/1981 | Stephens et al. | 422/62 |
| 4,533,641 A | 8/1985 | Holt | 436/43 |
| 4,619,902 A | 10/1986 | Bernard | |
| 4,882,098 A | 11/1989 | Weetman | |
| 4,896,971 A | 1/1990 | Weetman et al. | |
| 4,902,896 A | 2/1990 | Fertig, Sr. et al. | |
| 5,037,067 A | 8/1991 | Ray | |
| 5,047,212 A | 9/1991 | Blades et al. | 422/82.02 |
| 5,232,604 A | 8/1993 | Swallow et al. | |
| 5,271,900 A | 12/1993 | Morita | |
| 5,425,921 A | 6/1995 | Coakley et al. | 422/547 |
| 5,482,077 A | 1/1996 | Serafin | |
| 5,497,003 A | 3/1996 | Baliga et al. | 250/338.3 |
| 5,630,444 A | 5/1997 | Callaghan et al. | |
| 5,747,809 A | 5/1998 | Eckstrom | 250/345 |
| 5,835,216 A | 11/1998 | Koskinen | |
| 6,007,777 A | 12/1999 | Purcell et al. | |
| 6,114,700 A | 9/2000 | Blades | |
| 6,142,458 A | 11/2000 | Howk | |
| 6,375,900 B1 | 4/2002 | Lee-Alvarez et al. | |
| 6,447,725 B1 | 9/2002 | Inoue et al. | |
| 6,988,825 B2 | 1/2006 | Coville et al. | |
| 2004/0043499 A1 * | 3/2004 | Lee-Alvarez | 436/146 |

FOREIGN PATENT DOCUMENTS

| | | |
|---|---|---|
| CN | 2307958 Y | 2/1999 |
| CN | 1898562 A | 1/2007 |
| JP | 55-41836 | 3/1980 |
| JP | 60-244838 | 12/1985 |
| JP | 61-224981 | 10/1986 |
| JP | 63135858 | 6/1988 |
| JP | 1021352 | 1/1989 |
| JP | 1021355 | 1/1989 |
| JP | 1021356 | 1/1989 |
| JP | 1023156 | 1/1989 |
| JP | 64-51131 | 2/1989 |
| JP | 1049957 | 2/1989 |
| JP | 1049958 | 2/1989 |
| JP | 1318954 | 12/1989 |
| JP | 1318955 | 12/1989 |
| JP | 1318956 | 12/1989 |
| JP | 5080022 | 3/1993 |
| JP | 07-318555 | 12/1995 |
| JP | 11-101362 | 4/1999 |
| JP | 11101362 A | 4/1999 |
| JP | 2006-271431 | 10/2006 |
| JP | 2006-271431 A | 10/2006 |
| KR | 10-2001-0042378 | 5/2001 |

OTHER PUBLICATIONS

Aiken, George R., Chloride Interference in the Analysis of Dissolved Organic Carbon by the Wet Oxidation Method, Environ. Sci. Technol., vol. 26, No. 12, 1992, 2435-2439.
Koprivnjak et al., The Underestimation of Concentrations of Dissolved Organic Carbon in Freshwaters, Wat. Res., vol. 29, No. 1, 99-94, 1995. Leclercq et al., A supercritical oxidation system for the determination of carbon isotope ratios in marine dissolved organic carbon, Analytica Chimica Acta 370 (1998), 19-27.
Michio Nitta et al., Determination of TOC in Highly Purified Water by Wet Oxidation at High Temp. and High Pressure, 10th Annual Semiconductor Pure Water Conf, Feb. 26-28, 1991.
Wangersky, Peter J., Dissolved organic carbon methods: a critical review, Marine Chemistry, vol. 41, 1993, 61-74.
Williams et al., DOC subgroup report, Marine Chemistry, vol. 41, 1993, 11-21.

* cited by examiner

*Primary Examiner* — Christine T Mui
(74) *Attorney, Agent, or Firm* — David Silverstein; Andover-IP-Law

(57) ABSTRACT

Apparatus and methods for measuring the concentrations of organic and inorganic carbon, or of other materials, in aqueous samples are described, together with related, specially adapted components and sub-assemblies and related control, operational and monitoring systems.

56 Claims, 7 Drawing Sheets

CARBON MEASUREMENT IN AQUEOUS SAMPLES USING OXIDATION AT ELEVATED TEMPERATURES AND PRESSURES

CROSS-REFERENCE TO RELATED APPLICATIONS

This application claims benefit of the filing date of international application PCT/US08/10265 filed Aug. 29, 2008, which claims the benefit of the filing date of U.S. Provisional Application Ser. No. 60/967,576 filed Sep. 5, 2007.

FIELD OF THE INVENTION

This invention relates generally to methods and apparatus for making very precise, reliable and reproducible measurements of concentrations of organic, inorganic and total carbon present in aqueous samples. Such methods and apparatus may be used, for example, to determine the concentration of total organic carbon (TOC) in drinking water, raw water, wastewater, industrial process streams and the like. Such measurement may be utilized for various important commercial purposes, for example to optimize water purification processes, to detect spills, and to monitor compliance with environmental regulations. The methods and apparatus of this invention can generally be applied both to measuring discrete aqueous samples, such as those encountered in a laboratory environment, and to monitoring flowing streams to provide real-time concentration data.

The apparatus of this invention is able to rapidly and accurately measure carbon in samples containing high concentrations of salts and particulate material because the sample is oxidized at high temperatures and pressures, but is cooled to near ambient temperature before the sample exits the reactor. Since at least a portion of the sample leaves the reactor in the liquid phase, salts and particulate material are swept from the reactor and do not accumulate there. The conditions of the oxidation result in efficient oxidation and accurate carbon measurements that cannot be achieved in oxidations initiated by UV radiation or in wet chemical oxidation at lower temperatures. Furthermore, samples that are highly contaminated, especially with particulate material, are uniquely handled in the apparatus so that they do not cause excessive wear of sample syringes, valves, or other components, and do not settle out in the fluidic components. By maintaining the particulate material suspended in the liquid sample, plugging of fluidic components by particulates is minimized, and any organic material in those particulates is measured accurately.

BACKGROUND OF THE INVENTION

A. Overview

Total organic carbon is a well-established water quality parameter that quantifies the overall concentration of organic substances, all of which are typically regarded as contaminants, in an aqueous environment. Total organic carbon in an aqueous sample may be composed of either one or two components—dissolved organic carbon (DOC) and particulate organic carbon. The measurement of DOC is conventionally accomplished by filtering the water sample, commonly through a 0.45-μm filter, to remove particulate organic carbon prior to performing an analysis for DOC. The limitations of conventional apparatus and techniques for such analysis often lead to the result that only DOC is effectively measured, instead of TOC, because the particulates in a sample containing both forms of organic carbon typically cause errors in the measurement and plug fluid passages causing hardware failures.

In the following description, 'DOC' is used to refer to measurements in which the sample has first been filtered to remove particulates, while 'TOC' is used herein to refer to measurements in which the sample has not been filtered. In other respects, however, the following description is relevant to both DOC and TOC measurements.

In one known approach DOC and/or TOC, the organic compounds in an aqueous sample are oxidized to carbon dioxide ($CO_2$) and the $CO_2$ in the sample is then measured. In addition to organic carbon components, the water sample may initially contain $CO_2$ and other inorganic forms of carbon (e.g., in the form of bicarbonate and carbonate salts). Together, these forms of inorganic carbon are referred to herein as IC. Total carbon (TC) concentration in an aqueous sample is therefore the sum of the TOC and IC concentrations.

Because an aqueous sample following an oxidation step could contain $CO_2$ originating from both IC and TOC sources, the IC must be accounted for in some way to accurately measure TOC. One way to deal with IC is to remove the IC from the sample before the sample is oxidized. This is commonly done by acidifying the sample to convert carbonates and bicarbonates into free $CO_2$, and then sparging it with $CO_2$-free gas to remove that $CO_2$ originating from IC sources. It has been found, however, that at least some volatile organic compounds may be removed from the sample during such a sparging step. Thus, when the sparged sample is subsequently oxidized, the $CO_2$ produced is from the oxidation of the remaining (non-purgeable) organics in the sample, so this measurement is often referred to as the measurement of non-purgeable organic carbon (NPOC). Since many samples contain few, if any, purgeable organic compounds, the concentration of NPOC in those samples is typically considered to be essentially equal to the TOC concentration.

A second way of dealing with IC in a sample is to separately measure the TC and IC concentrations. When using this approach, the TOC concentration is calculated from the concentration difference, TC minus IC (TC−IC). One advantage of this approach is that the sample is not sparged so that purgeable organics are not lost thereby eliminating this source of measurement errors. As a result, the measurement of TOC by this "difference" approach is potentially more accurate.

When the approach to measuring carbon concentrations in aqueous samples is not constrained by requirements for regulatory compliance, a technician usually selects the parameter to be measured based on the time and resources required for each measurement, and the expected composition of the samples being monitored. Often, NPOC measurements are performed because they are relatively fast. Where it is necessary to accommodate a variable IC concentration, or where loss of purgeable organic carbon results in too large a discrepancy to be tolerated, TOC (or DOC) is measured by the difference approach, as described above.

In other cases, the samples may either contain IC concentrations that are known to be small compared to the TOC concentration, or the IC concentrations are relatively constant. In such cases, a technician may elect to measure TC because it is fast and it provides a sufficiently accurate indication of TOC trends for many common applications.

B. Identification of Related Prior Art

The following U.S. patents, each of which is incorporated herein by reference, are representative of pertinent prior art patents in the field of this invention and in related technical areas, such as oxidation of organic wastes: U.S. Pat. Nos. 3,296,435 (Teal '435); 3,700,891 (Luft '891); 3,958,945 (Takahashi '945); 4,619,902 (Bernard '902); 4,882,098 (Weetman '098); 4,896,971 (Weetman '971); 4,902,896 (Fertig '896); 5,037,067 (Ray '067); 5,232,604 (Swallow '604); 5,271,900 (Morita '900); 5,482,077 (Serafin '077); 5,630,444 (Callaghan '444); 5,835,216 (Koskinen '216); 6,007,777 (Purcell '777); 6,114,700 (Blades '700); 6,142,458 (Howk '458); 6,375,900 B1 (Lee-Alvarez '900); and 6,988,825 B2 (Colville '825).

The following technical publications, which are also incorporated herein by reference, are also representative of the pertinent prior art in this field: Aiken, G. R., "Chloride Interference in the Analysis of Dissolved Organic Carbon by the Wet Oxidation Method," *Environ. Sci. Technol.*, Vol. 26, No. 12, pp. 2435-2439; 1992; le Clercq, M.; van der Plicht, J. and Meijer, H. A. J., "A Supercritical Oxidation System for the Determination of Carbon Isotope Ratios in Marine Dissolved Organic Carbon," *Analyt. Chim. Acta*, Vol. 370(1), pp. 19-27; 1998; Eyerer, P., "TOC Measurements on the Basis of Supercritical Water Oxidation," AE-2e.1; Fraunhover-Gesellschaft zur Foerderung, Institut Chemische Technologie; Munich, Germany, http://www.ict.fraunhofer.de/english/projects/meas/onlan/index.html#a5; ISO-CEN EN 1484, "Water Analysis Guidelines for the Determination of Total Organic Carbon (TOC) and Dissolved Organic Carbon (DOC)," 1997; Koprivnjak, J-F, et al., "The Underestimation of Concentrations of Dissolved Organic Carbon in Freshwaters," *Water Research*, Vol. 29, No. 1, pp. 91-94, 1995; Menzel, D. W. and Vaccaro, R. F., "The Measurement of Dissolved Organic and Particulate Carbon in Seawater," *Limnology and Oceanography*, Vol. 9(1), pp. 138-142, 1964; Nitta, M.; Iwata, T.; Sanui, Y. and Ogawachi, T., "Determination of Total Organic Carbon in Highly Purified Water by Wet Oxidation at High Temperature and High Pressure," presented at Tenth Annual Semiconductor Pure Water Conference; Feb. 26-28, 1991, Santa Clara, Calif.; in Conference Proceedings, Balazs, M. K. (Ed.), pp. 314-320; Wangersky, P. J., "Dissolved Organic Carbon Methods: A Critical Review," *Marine Chem.*, Vol. 41, pp. 61-74, 1993; and, William, P. J. leB. et al., "DOC Subgroup Report," *Marine Chem.*, Vol. 41, pp. 11-21, 1993. These patents and technical publications are further referred to in the following description.

C. Prior Art Related to Sample Handling and Sparging

Many prior art analyzers, such as those described in Morita '900, Purcell '777 and Lee-Alvarez '900, draw the sample into a syringe pump. Those syringe pumps use rotary valves to connect the syringe to the sample, reagents, dilution water and other analyzer apparatus. Any salts and particulates in the sample contact the sealing surfaces of the valve and syringe. As particles settle onto those surfaces, they cause wear and premature leaking. Salts also dry on the surfaces and cause additional wear because the salt crystals are abrasive.

Efficient sparging has been a goal of certain of the prior art patents and publications. Takahashi '945, for example, describes a multi-stage sparger for use in TOC analyzers. Employing more than one stage improves the efficiency of the sparging process. However, the large internal volume of this device would make it difficult to flush out between uses with different samples that have widely different concentrations of contaminants.

Weetman '098, Weetman '971, and Howk '458 teach that sparging can be made more efficient by stirring the solution with rotating propellers. This modified sparging method would be complex to incorporate in an analytical instrument, however, because of the motor and rotating seals that would be required.

In some prior carbon analyzers that add reagents to the sample, mixing is facilitated by bubbling gas through the solution (for example, Purcell '777). As discussed above, however, some samples should be measured without sparging because sparging can remove volatile organics and thereby introduce an error into the measurements. However, no analyzer is known to incorporate a device that can be used to sparge certain samples when desired, while also mixing other samples with reagents without sparging. Further, in prior analyzers, when the sparging stops, any particulates in the solution settle to the bottom of the sparger. This makes it impossible to accurately measure organic material in the particles, and it increases the likelihood that fluid passages of the apparatus will become plugged.

D. Prior Art Related to Oxidation Techniques

It is well known in the art to oxidize organic carbon using wet chemical methods. For example, in the Menzel and Vacarro publication, the authors report measuring DOC and particulate organic carbon in seawater by oxidizing a 5 mL sample in a sealed glass ampoule that also contained the oxidizing agent potassium persulfate. The oxidation was achieved by heating the ampoule to 130° C. for 30 min. After the heating step, the ampoule was cooled, broken open, and the $CO_2$ contained inside it was measured using a non-dispersive infrared (NDIR) detector. Among other disadvantages, this method has the disadvantage that it involves many manual steps. Furthermore, the ampoules can break when they are heated or handled, raising concerns about loss of data and safety. This method would be impractical for real-time monitoring of process streams, or even laboratory analyses where many samples are to be analyzed each day.

Bernard '902 describes an instrument that automates the wet chemical oxidation method. The sample is acidified and a persulfate-containing reagent is added prior to the oxidation. $CO_2$-free gas is bubbled through the sample to remove the IC (in preparation for making an NPOC measurement) or to transfer it to a NDIR detector for measurement of the IC. The solution is then heated to 90 to 100° C. at ambient pressure to achieve oxidation of the organics. During the oxidation, the $CO_2$ is transferred to the NDIR detector where it is measured. The oxidation by persulfate at these temperatures is slow; in fact, the innovative aspect of Bernard '902 is the use of metal catalysts to increase the rate of the oxidation.

Another shortcoming of such wet chemical methods is that the oxidation of organics by prior wet chemical methods is incomplete, especially when the sample contains chloride [as reported for example in the publications of William, et al.; Wangersky; Koprivnjak, et al.; and Aiken]. When the oxidation is incomplete, the TOC measurement is inaccurate because not all of the organic carbon is measured.

Purcell '777 describes another analytical instrument that measures carbon in aqueous samples. In this case, the sample is acidified and an oxidizing reagent (a solution containing persulfate salts) is added to the sample. This mixing occurs in a syringe, and the resulting solution is then transferred to a sparger. After sparging, the syringe transfers the sample to a reactor where the solution is irradiated with ultraviolet (UV) radiation. In the presence of the UV radiation and the persulfate reagent, many organics in the sample are oxidized to $CO_2$, and the $CO_2$ is measured in a NDIR detector.

A problem with the oxidation of organics using UV radiation, as in Purcell '777, is that it is inefficient when the sample contains particulates. For example, one study reported that TOC analyzers that are based on UV oxidation detected less than 3% of the cellulose particles added to samples at an actual concentration of 20 mg C/L. By comparison, analyzers based on high-temperature catalytic oxidation (HTCO), as described below, on average detected 83.2% of the cellulose represented by cellulose particles.

To achieve more complete oxidation and, therefore, greater accuracy, analyzers were developed that oxidize organics using HTCO. Teal '435, for example, teaches that TOC in aqueous samples can be measured by injecting a portion of an IC-free sample into a catalytic reactor heated to around 900° C. The water vaporizes immediately, and organic materials are oxidized to $CO_2$ upon contact with the catalyst. A carrier gas (oxygen) transports the $CO_2$ out of the reactor to a NDIR detector.

Morita '900 and Lee-Alvarez '900 describe methods and apparatus that automatically acidify and sparge samples, oxidize organics using HTCO, and use NDIR detectors to measure the $CO_2$. In both of these approaches, the sample is mixed with acid in a syringe connected to a multi-port valve that directs fluids to other components. Morita '900 describes the sparging as being performed inside the syringe, while Lee-Alvarez '900 describes a separate sparger.

A shortcoming of all methods based on HTCO is that samples containing salts or particulate material will eventually plug the reactor because the water evaporates in the reactor, leaving nonvolatile salts and particulates behind. In addition, the reactor typically requires two hours or more to cool enough so that it can be safely removed and cleaned. Then, about another two hours are required for the reactor to heat back up to its operating temperature. This means that the instrument is out of service for an extended period whenever the reactor must be cleaned.

Other oxidation methods have also been reported. The Nitta et al. technical publication describes an analyzer in which the sample is mixed with sulfuric acid and sodium persulfate. IC is removed by sparging, and then a pump pressurizes a continuously flowing stream of the solution to 2.0 to 2.5 MPa (284 to 356 psig). The pressurized solution is heated in a reactor to 200° C., and the organics are oxidized to $CO_2$. The solution then flows through a flow restrictor (it is the flow through this restrictor that generates the upstream pressure as stated above). The $CO_2$ produced during the oxidation is removed by sparging and is measured using an infrared detector. Several Japanese patents describe additional aspects of the instrument as described above (JP63135858, JP1021352, JP1021355, JP1021356, JP1021356, JP1049957, JP1049958, JP1318954, JP1318955, JP1318956, and JP5080022). This method has the advantage that higher oxidation temperatures, presumably with more complete oxidation, can be achieved than if the oxidation were performed at ambient pressure. However, the apparatus has the disadvantage that particles and salts will rapidly plug the restrictor. Furthermore, the cost of such an apparatus is likely to be high because solution has to be pumped continuously against the backpressure generated by the restrictor.

Attempts to improve the efficiency of the oxidation also have included oxidizing samples under supercritical conditions (i.e., above 374° C. and pressures above 22.12 MPa). Le Clercq et al. reported measuring carbon isotope ratios in DOC. Between 500 and 1,000 mL of seawater were mixed with oxygen, pumped to a maximum pressure of 35 MPa, and forced through an alumina reactor heated to 650° C. Placing a 0.18 mm ID capillary downstream of the reactor and setting the flow rate at 2 mL/min produced the aforementioned pressure. The gases exiting the capillary were cooled to collect the $CO_2$ formed during the oxidation, and a mass spectrometer was used to measure the isotopes of carbon in the $CO_2$. A problem with this apparatus is that samples that contain particulates tend to plug the capillary. Such a problem was reported by le Clercq et al., and they installed a 2-µm filter ahead of the capillary in an attempt to mitigate the problem. However, in applications in which the apparatus must operate for long periods, even the periodic plugging of such a filter would create excessive maintenance and downtime. Another problem is the extremely high temperature and pressure at which the oxidation is made to occur. Appropriate hardware for such operating conditions is costly, and it is likely to corrode rapidly. The reactor described in this technical literature was made from alumina to minimize corrosion, but the structural characteristics of alumina make it unreliable. For this reason, the alumina reactor had to be mounted inside a metal shield for safety.

Eyerer reported another approach. The sample is first pumped through an electrochemical cell that generates the oxidizing agent. Then the sample passes through a reactor heated up to 600° C. and through a valve that creates a backpressure up to 26 MPa. The sample is oxidized at those conditions and then passes over a hydrophobic membrane. Some of the $CO_2$ diffuses through the membrane and is measured in a mass spectrometer. This apparatus suffers from the same types of corrosion, reliability, and cost shortcomings, however, that were discussed above for the le Clercq et al. approach.

Beyond applications in the measurement of organic carbon, as described above, rapid oxidation also has been a goal of developers of organic waste destruction systems. One way of achieving the desired rapid oxidation rates has been to perform the oxidation at near-critical and supercritical conditions. A variety of oxidizing agents have been employed, and one of the most economically attractive oxidizers is the oxygen in air. Swallow '604 teaches that if ozone, hydrogen peroxide, or salts containing persulfate, permanganate, nitrate, and other oxygen-containing anions are added to the liquid/air mixture, the oxidation rate is sufficiently rapid that the exothermic process operates without supplemental heating. This is an important consideration for large industrial processes, but it is much less important to analytical instrumentation because the hardware is much smaller.

Instead of oxidizing organics in a continuously flowing stream, batches of the sample could be heated. To do that requires that the batch be sealed in a container that is subsequently heated, and the best way of automatically sealing the container would be to use a valve that can withstand the pressure generated during heating. Many valves designed for high-pressure applications employ precision sealing surfaces. Ball valves require highly polished balls in packing glands to avoid leaks. Other high-pressure valves require metal-to-metal seals (for example, as described in Callaghan '444). Those valves are costly and subject to rapid wear by particles in the liquid.

A better method of achieving valve sealing in the presence of particulates is to use a softer seal that is resistant to abrasion. Serafin '077 teaches that elastomeric seals can be used in check valves at high pressure, and Ray '067 describes the use of O-rings to seal the ports in a plug valve. Both inventions have the disadvantage that the seals are not easily accessed for replacement when they become worn.

E. Prior Art Related to NDIR Detectors

NDIR detectors of $CO_2$ used as components of TOC analyzers commonly use a rotating chopper wheel to modulate the infrared (IR) radiation, and a pneumatic IR detector to measure the IR radiation that has not been absorbed by the $CO_2$ being measured. Luft '891 describes such a NDIR detector. Shortcomings of this technology include the fact that the chopper wheel mechanism is subject to failure, and irregularities in the size and orientation of the openings in the chopper wheel produce significant electrical noise in the measurement of $CO_2$.

To overcome the effects of temperature and pressure on NDIR response, detectors with built-in temperature and pressure compensation have been reported, such as in Fertig '896. An alternative approach to overcoming temperature effects is to use an IR detector that is relatively unaffected by temperature, such as a pyroelectric detector. Koskinen '216 describes a NDIR detector that electronically modulates the IR source to avoid problems with chopper wheels, and it uses a pyroelectric IR detector. However, this NDIR uses a costly Fabry-Perot interferometer to select the IR wavelength that is measured.

Blades '700 describes a NDIR detector designed specifically for use in a TOC analyzer. The IR source is an electrically modulated incandescent lamp with a pyroelectric IR detector. However, the use of an incandescent lamp limits the dynamic range and sensitivity of the NDIR because the modulation is limited to low frequencies.

Commonly, NDIR detectors use rectifier circuits and lowpass filters to produce a DC signal that is proportional to the average output of the IR detector. Shortcomings of this technology include the conversion of "noise" over a wide bandwidth into a part of the rectifier output signal. Additionally, the lowpass filter that averages the rectified waveform also impairs the ability of the NDIR to respond to rapidly changing $CO_2$ concentrations. Blades '700 reports an NDIR that uses two synchronous detectors, with each responding to opposite half-cycles of the signal from the IR detector. The use of two synchronous detectors improves the response time limitation of the rectifier circuit, but this approach still suffers from the shortcoming of mixing noise into the output signal.

Carbon measurement instruments commonly generate chlorine when the sample contains chloride ions. That chlorine would corrode many NDIR detectors, so scrubbers are used to remove the chlorine before it enters the NDIR (as, for example, in Lee-Alvarez '900 and Purcell '777). The scrubber is a consumable that adds to the operating cost and maintenance labor of those instruments.

These and other limitations of, and deficiencies in, the prior art approaches to IC, TOC and TC measurements are overcome in whole, or at least in part, by the methods and apparatus of this invention.

OBJECTS OF THE INVENTION

Accordingly, a general object of this invention is to provide methods and apparatus for determining the presence of and/or measuring one or more other elements, other than hydrogen and oxygen, e.g., an impurity, that may be present in an aqueous sample when at least one of such other elements may be present in organic form, inorganic form or both.

A more particular object of the present invention is to provide methods and related apparatus, which may be readily automated, for determining the presence of and/or measuring organic and/or inorganic carbon in one or a series of discrete aqueous samples.

Another principal object of the present invention is to provide methods and related automated apparatus for measuring and/or monitoring the concentrations of organic and/or inorganic carbon in one or more flowing aqueous streams.

Another object of this invention is to provide methods and related apparatus for measuring organic and inorganic carbon in one or a series of discrete aqueous samples and/or flowing streams that may contain particulates and salts.

Yet another object of this invention is to provide for the addition of reagents and, when needed, dilution water to a sample being tested in a way that particulates and salts in the sample do not plug fluid passages or cause excessive wear to syringe pump components.

Still another object of this invention is to provide for the effective transfer of particulates in an aqueous sample being analyzed into a sealable oxidation reactor in a substantially homogenous solution or suspension, so that carbon concentration measurements accurately reflect the amount of carbon in the particulate material.

Another object of this invention is to provide methods and related apparatus for oxidizing, reacting and/or decomposing organic material in an aqueous sample using a reactor that can be sealed while an aqueous sample inside the reactor is subjected to temperature and pressure conditions sufficient to cause oxidation, reaction and/or decomposition of the organic material in the sample.

A more specific object of this invention is to provide methods and related apparatus that oxidize the organic carbon in an aqueous sample substantially completely in a sealable reactor, so that the measurements of organic carbon accurately reflect all of the carbon whether present in dissolved and/or particulate form in the sample.

Yet another object of this invention is to provide methods and related apparatus that measure $CO_2$ derived from the organic and/or inorganic carbon in an aqueous sample in a way that is reliable, reproducible and essentially unaffected by variations in temperature, pressure, or concentrations of $CO_2$ in the ambient air.

Another object of this invention is to measure $CO_2$ derived from the organic and/or inorganic carbon in an aqueous sample over a wide range of concentrations, while rejecting "noise" or interferences that would limit $CO_2$ measurement accuracy at low concentrations and yet still responding quickly to rapid changes in the $CO_2$ concentration.

Still another object of this invention is to measure $CO_2$ derived from the organic and/or inorganic carbon in an aqueous sample while substantially avoiding corrosion of the measurement apparatus by chlorine or other oxidation products emanating from an oxidation reactor used in the measurement method.

These and other objects and advantages of this invention will be apparent from the following detailed description with reference to the attached drawings.

SUMMARY OF THE INVENTION

By contrast with the limitations of the prior art approaches to making such carbon concentration determinations in aqueous samples, as discussed above, the methods and apparatus of the present invention are uniquely capable of measuring all of the aforementioned parameters in samples that contain concentrations of TOC, dissolved solids, and particulates. In general a sample is drawn into the analyzer of this invention, reagents are added, and the sample is diluted as necessary. With the present invention, it is possible to completely avoid having the sample enter apparatus components that would be damaged by the dissolved solids or particulates in the sample. This invention also keeps the particulates suspended in the sample solution at least until it enters the oxidation reactor. This procedure therefore allows particulate organic carbon to be measured accurately, and it avoids additional maintenance labor and downtime that would otherwise be caused if particulates were allowed to settle out in the sparger and plug sample passages.

The oxidation of the organic carbon (or other organic material) in a known volume of sample processed according to this invention occurs in a reactor, which can alternately be sealed to contain a fluid therein at elevated temperature and pressure conditions or unsealed to introduce or remove a fluid sample. Such a sealable reactor is uniquely designed and adapted to be capable of handling samples that contain salts and particulates. In a representative invention embodiment, a known volume of sample is flowed into the sealable reactor, which initially is cool, through an open reactor inlet port. The reactor is then sealed and, after being sealed, is rapidly heated to temperature and pressure conditions at which the organic material in the sample is rapidly oxidized. Because the water in the aqueous sample cannot boil away in the sealed interior of the reactor, the sample (and the organic material in the sample) can be heated to relatively high temperatures and pressures. Furthermore, it has been found that, at the high temperature/pressure conditions attainable inside the sealed reactor of this invention, water in the aqueous sample can become a supercritical fluid that exhibits special properties including properties that facilitate the rapid oxidation of organic material.

When the oxidation of organic material is complete, the reactor is quickly cooled to near ambient temperature so as to condense a liquid reactor product. The reactor is then opened, and the oxidized sample exits the reactor through an open reactor outlet port in part as a liquid reactor product (taking with it the salts that were originally dissolved in it) together with a gaseous reactor product that will include organic material oxidation products such as $CO_2$. Particulates also are flushed out of the reactor. Because a liquid reactor product is recovered in this step, the salts and particulates do not accumulate in the reactor, and, as a result, maintenance and downtime are minimized.

The $CO_2$ in an oxidized sample coming from the reactor is measured in an innovative type of NDIR detector according to this invention that is reliable, stable, and has a wide dynamic range. These characteristics of the NDIR detector of this invention allow the analyzer to operate for long periods without recalibration.

The present invention has a particular advantage in that samples are not drawn into a syringe or its valving, where salts and particulates would cause leaks. Instead, the sample and the reagents are drawn into a length of tubing by means of a syringe that itself contains only clean dilution water. That dilution water also can be used to dilute samples that contain very high concentrations of organic carbon prior to further processing. In a preferred embodiment of this invention, the analyzer is capable of measuring up to about 1,000 ppm TOC in a sample without dilution of the sample, and up to about 50,000 ppm TOC in a sample if the sample is diluted (the only constraint here being the preferred sizes of the various apparatus components, with a larger apparatus being capable of handling even higher TOC concentrations with appropriate dilution).

The mixture or combination of sample and reagents (and dilution water when necessary) then enter a mixing device according to this invention that can both mix and sparge the solution/suspension. The mixing apparatus consists of a solenoid and a magnetic stirrer (stirring bar) that is coated with an inert polymer to prevent corrosion. The stirring bar may have protrusions on each end that help to agitate the sample mixture as the bar moves up and down in the chamber. This design requires no motors or rotating seals. The magnetic mixer of this invention has been found to unexpectedly improve the efficiency of the sparging when it is activated. Such an improvement is unexpected in view of the fact that the gas bubbles by themselves seem to agitate the solution vigorously during the sparging process. Less time is therefore required for essentially complete removal of IC when using the mixing/sparging apparatus of this invention, thus making the analysis faster.

Organic compounds are oxidized efficiently in a preferred embodiment of this invention at temperatures around 375° C. At this temperature, the oxidation of organics with persulfate, oxygen, or other oxidizers is rapid and substantially complete. We have found that there is no corrosion of the reactor and valves when they are constructed from titanium.

The reactor in the present invention is unusually reliable because it is heated only during the short period when a sample is actually being oxidized. The preferred reactor of this invention has a relatively small mass which allows it to be rapidly heated to oxidize the sample, and then rapidly be cooled back down to ambient temperature. The present invention can be put into service rapidly upon initial startup or after maintenance, thereby minimizing downtime.

In a preferred embodiment of the invention, the special high-pressure valves used at the inlet and outlet ports of the reactor tube include seals constructed of high-density polyethylene, polyvinylidene fluoride (PVDF), or elastomers such as ethylene propylene diene monomer (EPDM). The use of these materials allows the valves to seal reliably even when the sample being processed contains particulate material, and the cost of these valves is reduced because precision machining is not necessary. An unusual feature of the reactor valves according to this invention is that the seals can be easily and quickly replaced when they do become worn. In addition, the reactor valves of this invention are unlike any other known valves because each valve incorporates a bypass fluid path that allows the interior of each of the valves to be flushed clean when the reactor is sealed.

The present invention does not require costly high-pressure pumps or restrictors that would be plugged by particulates. It does not require the use of fragile ampoules, UV lamps that contain toxic mercury, or expensive catalysts. The completeness of oxidation is not degraded by the presence of chloride or particulate materials in the sample. Unlike HTCO reactors of the prior art, the present invention does not accumulate salts or particulates in the reactor, and maintenance on the reactor is minimal.

The NDIR detector according to the present invention is especially reliable because it has no moving parts, and it is constructed of materials that are compatible with oxidation products coming from the reactor, including chlorine. Unlike many other comparable instruments, with this invention no scrubbers are required to remove chlorine from the gas entering the NDIR.

The IR source utilized in this invention can be selected from among various types of infrared radiation sources, including incandescent light bulbs, thermal radiators, and electroluminescent diodes. The IR source in the preferred embodiment is a thin thermoresistive film that produces intense IR radiation, even when electrically modulated at high frequencies that permit low concentrations of $CO_2$ to be measured with precision.

The IR detector utilized in this invention can also be selected from among various types of infrared radiation detectors, including bolometric, thermoelectric, and photoelectric types. The pyroelectric IR detector in a preferred invention embodiment is one that is relatively immune to temperature changes. To further eliminate the effects of temperature, the IR source and IR detector may be controlled at fixed temperatures in a preferred embodiment. The IR source and IR detector are preferably mounted in chambers that are flushed with $CO_2$-free gas, thereby preventing response variations due to changes in the ambient $CO_2$ concentration. The response of the NDIR may also be adjusted to compensate for changes in the pressure of the $CO_2$.

Multiple wavelengths can be used to measure $CO_2$ in the NDIR of this invention, and the selected wavelength can be implemented in any of several ways, including the use of optical filters and the use of IR sources that emit radiation of the desired wavelengths (e.g., light-emitting diodes). When optical filters are used, they can be located in various locations within the NDIR detector. In a preferred embodiment, a nominal wavelength of about 4.26 µm is used for $CO_2$ measurement, and the optical filter that is employed to eliminate other wavelengths is part of the IR detector, and typically is located immediately in front of its sensing element.

In one illustrative embodiment of this invention, a sample is drawn into the instrument using a syringe pump. Instead of the sample entering the syringe, however, the sample enters a length of tubing that can be easily and inexpensively replaced if it ever becomes plugged or permanently contaminated by a sample. The tubing is advantageously coiled to reduce the amount of space it occupies inside the instrument.

The syringe is also arranged and/or connected so as to sequentially (but in any desired order) draw acid and oxidizer reagents and sample into the coil of tubing. If the concentration of the organic carbon in the sample is very large, dilution water can be drawn in, too, as discussed above. The total volume of liquid drawn into the tubing is known by monitoring the operation of the syringe pump, so dilution ratios can be controlled precisely.

The several fluids in the coil tubing can then be discharged to a mixing location in the apparatus, such as a chamber that combines a mixer and sparger. The sample and other fluids in the mixing chamber can be thoroughly mixed and sparged to measure NPOC, or mixed without sparging when TC or IC is being measured. The mixing action keeps particulates suspended substantially homogenously in solution or suspension, so the solution/suspension can be accurately measured without plugging the mixing chamber or the tubing connected to it.

A portion of the sample mixture from the mixing chamber is then flowed to a reactor tube of an oxidization reactor where it is sealed in an interior region of the reactor tube. Reactor valves as described above, and able to withstand high pressures, seal each end of the reactor tube. The tube is then heated to temperatures between about 150° C. and 650° C., or preferably between about 300° C. and 400° C., and more preferably between about 350° C. and 390° C. The tube is heated for approximately one to thirty minutes, e.g., preferably for about two to four minutes. At the end of that period, the heater is turned off, and a fan blows ambient air over the reactor tube to rapidly cool it to near ambient temperature. The valves are opened, and a $CO_2$-free carrier gas is used to blow the reactor liquid and reactor gas from the interior region of the reactor tube. The liquid and gas reactor products are separated, and the carrier gas transfers the gaseous oxidation products, including the $CO_2$, to a chemical detector, e.g., an NDIR detector, in accordance with this invention for carbon measurement.

In the NDIR, IR radiation is emitted from an IR source that is electrically modulated at a suitable frequency, in one preferred invention embodiment at 55 Hz. In one preferred embodiment, the IR source is maintained at a suitable fixed temperature (e.g., about 65° C.) in a chamber that is purged by $CO_2$-free gas. The IR radiation from the source is collimated by a lens and passes through the gas (a combination of the gaseous oxidation products and carrier gas) flowing from the reactor. Any $CO_2$ present in the gas flowing through the NDIR absorbs IR at wavelengths around 4.26 µm, e.g., 4.26 µm±0.2 µm. The IR radiation that is not absorbed by $CO_2$ then passes through a second lens that focuses it onto an IR detector, In one preferred embodiment, a filter is located on the face of this IR detector to block IR at wavelengths other than 4.26 µm from reaching the pyroelectric detector element, and the IR detector is mounted in a chamber that is purged with $CO_2$-free gas, and is maintained at a fixed temperature (e.g., about 55° C.).

The NDIR electronic circuitry drives the IR source at the modulation frequency, and the IR detector converts the infrared light that it receives back into an electrical signal, which signal is attenuated by any $CO_2$ present in the gas being measured. The NDIR electronic circuitry conditions this signal with a bandpass filter, and then converts this analog signal to digital with an analog-to-digital converter that samples the waveform many times per modulation cycle (in one preferred invention embodiment, at 100 waveform samples per modulation cycle). The NDIR electronic circuitry also uses digital signal processing techniques to perform further bandpass filtering and to measure the amplitude of the received signal. From this amplitude, the NDIR electronic circuitry calculates and reports the $CO_2$ concentration in the gas flowed from the reactor.

In a more specific apparatus embodiment, this invention comprises an analytical instrument for measuring carbon in a liquid sample, wherein the instrument comprises in combination: a sample inlet; a pump to draw said sample and, optionally, other materials into the apparatus; a mixing chamber; a source of sparging and/or carrier gas and a gas flow control system; an oxidation reactor, wherein the oxidation reactor can be sealed at each end to contain a sample mixture; a heater; a fluid pumping system to transport liquids and mixtures of gases and liquids through the aforementioned components; and a $CO_2$ detector to measure $CO_2$ in the reactor product coming from the reactor.

In another specific embodiment, this invention comprises an analytical instrument having the several elements and components as described above, and further includes an acidic reagent inlet.

In another specific embodiment, this invention comprises an analytical instrument having the several elements and components as described above, and further includes an oxidizer reagent inlet.

In another specific embodiment, this invention comprises an analytical instrument having the several elements and components as described above, and further includes a dilution water inlet.

In still another specific embodiment, this invention comprises an analytical instrument having the several elements and components as described above, and further includes a fan or blower to cool the reactor.

In still another specific embodiment, this invention comprises an analytical instrument having the several elements and components as described above, and further includes a mixing or mixing/sparging chamber that is configured in a way that relatively easily permits a sparging gas to be bubbled through a solution or liquid suspension contained in the mixing/sparging chamber.

In yet another specific embodiment, this invention comprises an analytical instrument having the several elements and components as described above, and further includes a valve or comparable flow control element for directing or channeling gas coming from the mixing/sparging chamber (after it has been bubbled through a solution or liquid suspension, e.g., an acidified sample mixture, contained in the chamber) to the $CO_2$ detector.

In another specific embodiment, this invention comprises an analytical instrument having the several elements and components as described above, and further includes a NEAR detector designed to measure a wide range of $CO_2$ concentrations using AC signal processing for noise rejection/filtering and for signal amplitude measurements.

In another specific embodiment, this invention comprises automating an analytical instrument having the several elements and components as described above using electronic and/or computer control systems as herein described.

In another specific embodiment, this invention comprises methods of operating and controlling an analytical instrument having the several elements and components as described above.

In a general method embodiment, a method according to this invention comprises the sequential steps of: drawing a selected volume of sample into a sample-handling portion of the analytical system; adding suitable volumes of an acid reagent (of a known acidity or acid concentration) and, depending on the type of carbon being measured, also of an oxidizer reagent (of a known concentration) relative to the volume of sample; possibly diluting the sample/acid/oxidizer mixture with low or essentially zero TOC dilution water if desired; mixing the sample, acid, oxidizer (if present) and dilution water (if any) to form a substantially homogenous solution or liquid suspension; if NPOC is to be measured, sparging the acidified solution/suspension with $CO_2$-free gas (provided, for example, by a gas control assembly of the system) while controlling the flow rate of the sparge gas to ensure that IC in the sample is substantially completely removed; alternatively, if TC or IC is to be measured, mixing but not sparging the solution/suspension; transferring a portion of the homogenous mixed/sparged solution/suspension to an oxidation reactor; if NPOC or TC is to be measured, heating the portion of the solution/suspension after the reactor is sealed to oxidize organic compounds in the portion of the solution/suspension, then cooling it to near room temperature; using a stream of carrier gas from a gas control assembly to transfer the liquid and gaseous reactor products in the reactor to a gas/liquid separator; separating the liquid from the gas, and removing the separated liquid from the gas/liquid separator; flowing the gaseous reactor product (containing the $CO_2$) from the gas/liquid separator to an NDIR detector; measuring the $CO_2$ in the gaseous reactor product using the NDIR detector; and, optionally, after the $CO_2$ in the gaseous reactor product is measured, flowing the gaseous reactor product back through the gas/liquid separator and then venting it to the atmosphere.

In another apparatus embodiment, an apparatus according to this invention comprises the following apparatus elements or components in combination; a sample-handling unit comprising multiple valves and a syringe connected through a three-way valve to both a coil of tubing and a reservoir containing low-TOC dilution water, wherein the internal volume of the coil of tubing is larger than the internal volume of the syringe; a pump to draw sample from a sample source and deliver it by a conduit connection to a six-way fluid interconnection element; a mixing/sparging chamber connected to the coil of tubing, said chamber including a sparging element for sparging $CO_2$-free gas through a solution/suspension in the chamber; a source of compressed $CO_2$-free gas connected to the sparging element and a gas control module to control the flow and pressure of such gas; optionally, a valve and conduit to direct gas emerging from the mixing/sparging chamber through a gas/liquid separator and then to an NDIR detector; a pump and associated conduit to transfer at least a portion of the mixed/sparged solution/suspension from the mixing/sparging chamber to a sealable reactor; a source of carrier gas connected to the reactor and, via the gas/liquid separator, to an in-line filter and then to the NDIR detector; a heater and a fan associated with the reactor; and an associated automated control system comprising electrical connections and operational software adapted to operate fluid valves and other system control elements according to a predetermined sequence and/or timing or, alternatively, in accordance with feedback received from various system monitors.

In another specific apparatus embodiment, an NDIR detector in accordance with this invention comprises three chambers: a first chamber containing an IR source; a second chamber centrally located and comprising an optical path through which carrier gas and a gaseous reactor product including $CO_2$ flow; and a third chamber containing the IR detector, wherein said first and third chambers are designed to be flushed with a $CO_2$-free gas during measurements.

In another specific apparatus embodiment, a mixer/sparger element in accordance with this invention comprises a top section that includes a liquid inlet and a sparge gas outlet, a bottom section that includes an inlet port for sparge gas and a liquid outlet, and a middle section containing a magnetic stirrer component, the middle section being located inside a solenoid coil which can be activated by passing a series of current pulses through it causing the magnetic stirrer component to move up and down inside the middle section.

In another specific apparatus embodiment, an apparatus in accordance with this invention comprises a pair of high-pressure reactor valves, each such valve comprising a polymeric or elastic seal attached to a plunger that moves back and forth inside a valve body when an associated motor is activated, and wherein the rear portion of the seal retains two O-rings so as to seal the interior of the housing, and wherein the front portion of that seal plugs a reactor opening (a reactor inlet or a reactor outlet) when the valve is in a closed position.

In another specific apparatus embodiment, an IR source for the NDIR in accordance with this invention comprises a modulated, thin-film IR radiator.

In another specific apparatus embodiment, an NDIR detector in accordance with this invention comprises a pyroelectric sensor element, with the preferred embodiment having a pyroelectric sensor constructed from lithium tantalate.

Even more specifically, the present invention comprises the following embodiments:

1. An analytical instrument comprising in combination: a liquid sample inlet; a fluid transport system for drawing a known volume of a liquid sample into the instrument and for transporting liquids and gases to and through the components of the instrument; a reactor that can alternately be opened, to introduce a sample or to discharge a reactor product, or sealed to heat treat a sample inside the reactor to produce a reactor product; a reactor heating unit that can be turned on during a reactor heating cycle and turned off during a reactor cooling cycle; a reactor cooling unit that can be turned on during a reactor cooling cycle and turned off during a reactor heating cycle; a source of gas and a gas flow control system in communication with the fluid transport system; and, a chemical detector to measure a chemical component of the reactor product.

2. The instrument of paragraph 1 further comprising a fluid pumping system in communication with the fluid transport system.

3. The instrument of paragraph 1 further comprising one or more additional inlets selected from an acid reagent inlet, an oxidizer reagent inlet and a dilution water inlet.

4. The instrument of paragraph 1 further comprising a mixing/sparging chamber upstream from the reactor where a combination of a liquid sample and one or more other liquids can be either mixed or mixed and simultaneously sparged with sparge gas.

5. The instrument of paragraph 1 wherein the chemical detector comprises a detector for carbon, nitrogen or sulfur oxidation products downstream of the reactor.

6. The instrument of paragraph 1 wherein the chemical detector comprises a non-dispersive infrared (NDIR) detector downstream of the reactor.

7. The instrument of paragraph 6 wherein the NDIR includes an optical filter specific to the wavelength of IR radiation absorbed by the chemical component to be measured.

8. The instrument of paragraph 7 wherein the optical filter is specific to carbon oxidation products.

9. The instrument of paragraph 7 wherein the optical filter is specific to $CO_2$.

10. The instrument of paragraph 6 further comprising a gas/liquid separator between the reactor and the NDIR detector to remove liquid from the reactor product.

11. The instrument of paragraph 1 further comprising an AC signal processing element effective for noise rejection/filtering and signal amplitude measurements.

12. The instrument of paragraph 1 further comprising an electronic/computer automated control system.

13. An analytical instrument comprising: a sample-handling unit comprising multiple valves and a syringe connected through a three-way valve to both a coil of tubing and a reservoir containing low-TOC dilution water, wherein the volume of the coil is at least as large as the volume of the syringe; a pump component effective to draw sample from a sample source and deliver it by a conduit connection to a fluid interconnection element; a mixing/sparging chamber connected to the coil of tubing, said chamber including a sparging element for sparging $CO_2$-free gas through a solution/suspension in the chamber; a source of compressed $CO_2$-free gas connected to the sparging element and a gas control module to control the flow and pressure of such gas; a pump component and associated conduit to transfer at least a portion of the solution/suspension from the mixing/sparging chamber to a sealable reactor; a heater and a fan associated with the reactor; a source of carrier gas connected to the reactor; a conduit downstream of the reactor carrying the reactor product sequentially through a gas/liquid separator, an in-line filter, and then to a $CO_2$ detector; and an associated automated control system comprising electrical connections and operational software adapted to operate fluid valves and other system control elements according to a predetermined sequence and/or timing or, alternatively, in accordance with feedback received from various system monitors.

14. The instrument of paragraph 13 further comprising a valve and a conduit for carrying sparge gas emerging from the mixing/sparging chamber through the gas/liquid separator to the $CO_2$ detector.

15. An analytical method comprising the following sequential steps: drawing a known volume of sample into a sample-handling portion of an analytical system; adding suitable volumes of one or more chemical reagents relative to the volume of sample; mixing the sample and chemical reagents to form a substantially homogenous solution or suspension; transferring a portion of the homogenous solution/suspension to a reactor; sealing the reactor; treating the solution/suspension in the sealed reactor to form a reactor product; bringing the reactor and the reactor products to about ambient temperature; opening the reactor and, using a stream of carrier gas, transferring the liquid and gaseous reactor products from the reactor to a gas/liquid separator; separating the liquid reactor product from the gaseous reactor product; flowing the gaseous reactor product from the gas/liquid separator to a chemical detector; and, measuring a chemical component in the gaseous reactor product using the detector.

16. The method of paragraph 15 wherein the chemical reagents are selected from acid and oxidizer.

17. The method of paragraph 15 further including the step of adding dilution water to the sample and chemical reagents.

18. The method of paragraph 15 wherein the step of mixing the sample and chemical reagents also includes simultaneously sparging the solution/suspension with a sparge gas.

19. The method of paragraph 18 further comprising the step of monitoring the progress of the sparging step by flowing the sparge gas from the mixing/sparging step to the chemical detector for analysis.

20. The method of paragraph 15 wherein the solution/suspension includes organic materials and is heated in the reactor to a temperature between about 150° C. to about 650° C. in the reactor step substantially to oxidize the organic materials.

21. The method of paragraph 15 wherein the solution/suspension is heated to supercritical fluid temperature/pressure conditions in the reactor step.

22. The method of paragraph 15 wherein the solution/suspension is heated to a temperature of about 100° C. or less in the reactor step.

23. The method of paragraph 15 wherein the chemical detector is specific to a material selected from carbon, nitrogen and sulfur oxidation products.

24. The method of paragraph 15 wherein the chemical detector is a $CO_2$ detector.

25. The method of paragraph 15 wherein the chemical detector is a non-dispersive infrared (NDIR) detector.

26. The method of paragraph 25 wherein the NDIR includes an optical filter specific to the wavelength of IR radiation absorbed by the chemical component to be measured.

27. The method of paragraph 26 wherein the optical filter is specific to $CO_2$.

28. The method of paragraph 15 further wherein an AC signal processing element is used for noise rejection/filtering and signal amplitude measurements.

29. The method of paragraph 15 further wherein the analysis is automated by an electronic/computer automation control system.

30. The method of paragraph 15 further comprising the step of determining a concentration of a chemical component in the sample using a mathematical formula to correlate a response of the chemical detector to the gaseous reactor product with the concentration of the chemical component.

31. Apparatus for treating an aqueous sample containing organic material comprising:
  (a) a reactor having reactor inlet and outlet ports and a reactor interior for containing an aqueous sample under above-ambient temperature and pressure conditions;
  (b) high-pressure fluid reactor valve members at said reactor inlet and outlet ports, said reactor valve members allowing fluid flow respectively into or out of the reactor interior when in an open-valve mode or, alternatively, sealing the reactor interior when in a closed-valve mode;

(c) a reactor heater system adapted for rapidly and cyclically heating the reactor interior to above-ambient temperature conditions where an aqueous sample is sealed in the reactor interior; and, (d) a reactor cooling system adapted for rapidly and cyclically cooling the reactor interior and an aqueous sample sealed in the reactor interior following a heating cycle.

32. The apparatus of paragraph 31 wherein the reactor heating system is able to heat the reactor interior and an aqueous sample sealed in the reactor interior to a temperature of about 150° C. to about 650° C., while the reactor interior and the reactor valve members maintain the sample under sealed conditions.

33. The apparatus of paragraph 31 wherein the reactor heating system is able to heat the reactor interior and an aqueous sample sealed in the reactor interior to temperature and pressure high enough to generate supercritical fluid conditions inside the reactor interior, while the reactor interior and the reactor valve members maintain the sample under sealed conditions.

34. The apparatus of paragraph 31 wherein each of the reactor valve members comprises a valve housing having a main fluid inlet and a main fluid outlet, a moveable valve plunger element inside the valve housing, a front portion of the valve plunger element comprising a polymeric or elastic plunger seal member having a section sized and shaped to mate with and plug the main fluid outlet when the valve plunger element is in an advanced position, and to unseal the main fluid outlet when the valve plunger element is in a retracted position.

35. The apparatus of paragraph 34, the valve member further comprising a motor for alternately advancing or retracting the valve plunger element.

36. The apparatus of paragraph 34, the valve housing further comprising a purge gas inlet and a purge gas outlet whereby a purge gas can be flowed through the interior of the valve housing while the valve plunger element is sealing the main fluid outlet.

37. The apparatus of paragraph 31 wherein the reactor heater system comprises a hollow tubular heating element with the reactor in the hollow interior of the heating element.

38. The apparatus of paragraph 31 wherein the reactor cooling system comprises a fan located proximate to the reactor and oriented to blow ambient air along the exterior of the reactor.

39. The apparatus of paragraph 37 wherein the tubular heating element is open at each end, and further wherein the reactor cooling system comprises a fan located proximate to one open end of the heating element and oriented to blow ambient air through the hollow interior of the heating element and along the exterior of the reactor.

40. Apparatus for mixing an aqueous sample containing particulate material with one or more other liquid components, said apparatus comprising:

(a) a sealed tubular mixing container having a liquid inlet/gas outlet section at a first container end, said liquid inlet/gas outlet section including a sample inlet and a sparge gas outlet; a liquid outlet/gas inlet section at a second container end, said liquid outlet/gas inlet section including a sparge gas inlet and a sample outlet; and, between said liquid inlet/gas outlet section and said liquid outlet/gas inlet section, a fluid mixing region;

(b) a magnetically activatable stirrer element inside said fluid mixing region;

(c) an annular solenoid coil surrounding at least a portion of said fluid mixing region, said solenoid coil being activatable by a series of electric current pulses to move the stirrer element inside the fluid mixing region; and, (d) a porous gas disperser located between the sparge gas inlet and the fluid mixing region.

41. The apparatus of paragraph 40 wherein the stirrer element is coated with a corrosion-resistant outer layer.

42. The apparatus of paragraph 40 wherein the gas disperser has gas pores with a pore size ranging from about 1 min to about 0.125 in.

43. The apparatus of paragraph 40 wherein the stirrer element is activatable independently of whether sparge gas is being supplied to the fluid mixing region.

44. A purgeable fluid sealing valve apparatus comprising:

(a) a valve housing having a main fluid inlet and a main fluid outlet;

(b) a moveable plunger element inside the valve housing, a front portion of the valve plunger element comprising a plunger seal member sized and shaped to be seated on and plug the main fluid outlet when the valve plunger element is in an advanced position, and to unseal the main fluid outlet when the plunger is in a retracted position; and, (c) the valve housing further comprising a valve purge gas inlet and a valve purge gas outlet whereby a purge gas can be flowed through the interior of the valve housing while the valve plunger element is sealing the main fluid outlet.

45. The fluid sealing valve apparatus of paragraph 44 wherein said plunger seal member comprises a polymeric or elastic member.

46. The fluid sealing valve apparatus of paragraph 44 further wherein an exterior wall of the valve plunger element is adapted to seat one or more O-ring seals.

47. The fluid sealing valve apparatus of paragraph 44 further comprising a conduit connection from a source of purge gas to the valve purge gas inlet.

48. The fluid sealing valve apparatus of paragraph 44 further comprising a motor for alternately advancing or retracting the valve plunger element.

49. A purgeable non-dispersive infrared (NDIR) detector apparatus comprising:

(a) an IR source chamber comprising an IR source chamber purge gas inlet and a purge gas outlet, and containing an infrared radiation source;

(b) an IR detector chamber comprising an IR detector chamber purge gas inlet and a purge gas outlet, and containing an infrared detector; and, (c) between the IR source chamber and the IR detector chamber, an optical path chamber having an optical chamber gas inlet port at a first end of the optical path chamber and an optical chamber gas outlet port at a second end of the optical path chamber.

50. The NDIR apparatus of paragraph 49 further comprising a first compartment separation lens that isolates the IR source chamber from the optical path chamber, and a second compartment separation lens that isolates the IR detector chamber from the optical path chamber.

51. The NDIR apparatus of paragraph 49 further comprising an optical filter mounted in the infrared detector in front of the sensing element of the detector.

52. The NDIR apparatus of paragraph 51 wherein the optical filter is a 4.26 μm±0.2 μm filter.

53. The NDIR apparatus of paragraph 49 further comprising an electronic control system for automating operation of the apparatus, comprising:

(a) a driver to actuate the IR source at the modulation frequency;

(b) a bandpass filter to pass the infrared detector signal content at the modulation frequency;

(c) an analog-to-digital converter to sample the output of the bandpass filter many times during each modulation cycle; and, (d) digital signal processing elements to further bandpass filter the samples from the analog-to-digital converter, and to calculate the amplitude of the resulting AC signal.

54. The NDIR apparatus of paragraph 49 further comprising an electronic control system for automating operation of the apparatus.

55. The NDIR apparatus of paragraph 49 further comprising conduit connections from a source of purge gas to the IR source chamber purge gas inlet and to the IR detector chamber purge gas inlet.

56. The NDIR apparatus of paragraph 49 wherein the IR source comprises a modulated, thin-film IR radiator.

57. The NDIR apparatus of paragraph wherein the IR detector comprises a pyroelectric, lithium tantalate sensor element.

58. A sample/reagent handling apparatus comprising:

(a) separate sources of one or more liquids selected from an aqueous solution/suspension containing at least an impurity, dilution water, oxidizing reagent, and acid;

(b) conduit connections between the sources of the aqueous solution/suspension, oxidizing reagent and acid and a first end of a length of holding tubing, and a dilution water conduit connection between the dilution water source and a second end of the tubing;

(c) a calibrated syringe in fluid communication with the dilution water conduit connection, the syringe having an internal volume that is equal to or less than the internal volume of the tubing;

(d) a conduit connection between the first end of the tubing and a mixing device; and, (e) fluid valves along each of the conduit connections such that the syringe can be used to separately draw measured volumes of oxidizing reagent, acid and aqueous solution/suspension into the first end of the tubing by drawing dilution water from the second end of the tubing into the syringe, followed by discharging the dilution water in the syringe back into the second end of the tubing in order to transfer the liquids held in the first end of the tubing to the mixing device.

59. The sample/reagent handling apparatus of paragraph 58 further comprising a multi-way fluid hub located along the conduit connections between the aqueous solution/suspension, oxidizing reagent and acid sources and the first end of the tubing.

60. The sample/reagent handling apparatus of paragraph 58 wherein the mixing device comprises a mixing chamber in which the liquids transferred from the first end of the tubing can be mixed, or sparged with sparge gas, or mixed and sparged simultaneously.

61. The sample/reagent handling apparatus of paragraph 60 wherein the mixing device comprises:

(a) a sealed tubular mixing container having a liquid inlet/gas outlet section at a first container end, said liquid inlet/gas outlet section including a sample/reagent inlet and a sparge gas outlet; a liquid outlet/gas inlet section at a second container end, said liquid outlet/gas inlet section including a sparge gas inlet and a sample mixture outlet; and, between said liquid inlet/gas outlet section and said liquid outlet/gas inlet section, a fluid mixing region;

(b) a magnetically activatable stirrer element inside said fluid mixing region;

(c) an annular solenoid coil surrounding at least a portion of said fluid mixing region, said solenoid coil being activatable by a series of electric current pulses to move the stirrer element inside the fluid mixing region; and, (d) a porous gas disperser located between the sparge gas inlet and the fluid mixing region.

62. Liquid treatment apparatus for treating an aqueous sample containing a non-aqueous component to prepare the sample for a measurement of the non-aqueous component, said apparatus comprising a sample/reagent handling apparatus according to paragraph 61 in combination with a reactor apparatus comprising:

(a) a reactor having reactor inlet and outlet ports and a reactor interior for containing an aqueous sample under above-ambient temperature and pressure conditions;

(b) high-pressure fluid reactor valve members at said reactor inlet and outlet ports, said reactor valve members allowing fluid flow respectively into or out of the reactor interior when in an open-valve mode or, alternatively, sealing the reactor interior when in a closed-valve mode;

(c) a reactor heater system adapted for rapidly and cyclically heating the reactor interior to above-ambient temperature conditions where an aqueous sample is sealed in the reactor interior;

(d) a reactor cooling system adapted for rapidly and cyclically cooling the reactor interior and an aqueous sample sealed in the reactor interior following a heating cycle; and, (e) a mixing device/reactor conduit connection between the sample mixture outlet of said mixing device and the fluid reactor valve member at said reactor inlet port.

63. Analytical apparatus for measuring a non-aqueous component of an aqueous sample wherein at least a portion of the non-aqueous component may be present in the form of an organic material, said apparatus comprising a liquid treatment apparatus according to paragraph 62 in combination with a non-dispersive infrared (NDIR) detector apparatus comprising:

(a) an IR source chamber comprising an IR source chamber purge gas inlet and a purge gas outlet, and containing an infrared radiation source;

(b) an IR detector chamber comprising an IR detector chamber purge gas inlet and a purge gas outlet, and containing an infrared detector;

(c) between the IR source chamber and the IR detector chamber, an optical path chamber having an optical chamber gas inlet port at a first end of the optical path chamber and an optical chamber gas outlet port at a second end of the optical path chamber; and, (d) a reactor/NDIR conduit connection between the fluid reactor valve member at said reactor outlet port and the optical chamber gas inlet port of the NDIR detector.

64. The analytical apparatus of paragraph 63 further comprising a gas/liquid separator along the reactor/NDIR conduit connection to remove liquid components of the product of the reactor prior to reaching the NDIR.

65. The analytical apparatus of paragraph 63 further comprising a gas supply system that provides $CO_2$-free carrier gas to the reactor to transport reactor gas products along the reactor/NDIR conduit to the NDIR.

66. The analytical apparatus of paragraph 65 wherein each of the fluid reactor valve members comprise:

(a) a valve housing having a main fluid inlet and a main fluid outlet;

(b) a moveable plunger element inside the valve housing, a front portion of the valve plunger element comprising a plunger seal member sized and shaped to be seated on and plug the main fluid outlet when the valve plunger element is in an advanced position, and to unseal the main fluid outlet when the plunger is in a retracted position; and, (c) the valve housing further comprising a valve purge gas inlet and a valve purge gas outlet whereby a purge gas can be flowed through the interior of the valve housing while the valve plunger element is sealing the main fluid outlet; and, further wherein there is a conduit connection from the gas supply system to the valve purge gas inlet.

67. The analytical apparatus of paragraph 66 wherein there are conduit connections between the gas supply system and the IR source chamber purge gas inlet and the IR detector chamber purge gas inlet.

68. A method for treating an aqueous sample containing organic material, the method comprising the steps of:

(a) mixing a known volume of the aqueous sample with one or more other liquids selected from oxidizer, acid and dilution water to form a sample mixture;

(b) flowing at least a portion of the sample mixture into the interior of a reaction vessel which is at substantially ambient conditions, said reactor vessel being adapted to be alternately and repeatedly opened and sealed at reactor inlet and outlet ports;

(c) sealing the portion of sample mixture in the interior of the reaction vessel;

(d) rapidly heating the interior of the reaction vessel and the sample mixture portion inside to temperature and pressure substantially above ambient conditions and for a time sufficient substantially to oxidize the organic material and form a reactor product;

(e) stopping the heating step and then rapidly cooling the interior of the reaction vessel and the reactor product inside to substantially ambient conditions to form cooled liquid and gaseous reactor products; and, (f) opening the reaction vessel and removing the cooled liquid and gaseous reactor products from the reactor interior.

69. The method of paragraph 68 wherein the reactor interior is heated to a temperature between about 150° C. to about 650° C. in step (d).

70. The method of paragraph 68 wherein the reactor interior is heated to temperature and pressure high enough to generate supercritical fluid conditions in step (d).

71. The method of paragraph 68 wherein the reactor interior is heated to a temperature of about 100° C. or less in step (d).

72. The method of paragraph 68 wherein the reaction vessel is positioned in the hollow interior of a tubular heating element which is turned on to effect the heating step (d).

73. The method of paragraph 68 wherein the heating step (d) is completed in about 30 minutes or less.

74. The method of paragraph 68 wherein the heating step (d) is completed in about 4 minutes or less 75. The method of paragraph 68 wherein the reaction vessel is cooled in cooling step (e) by blowing ambient air over the exterior of the reaction vessel.

76. The method of paragraph 68 wherein the reaction vessel is sealed in step (c) by closing purgeable high-pressure reactor valves at the reactor inlet and outlet ports, the method additionally comprising the step of flowing a $CO_2$-free purge gas through the respective interiors of the reactor valves while the reaction vessel is sealed.

77. The method of paragraph 68 further comprising the step of flowing $CO_2$-free carrier gas through the interior of the reaction vessel as a part of step (f).

78. A method for treating the combination of an aqueous sample containing particulate material and one or more other liquid components to form a substantially homogeneous and, optionally, gas-free liquid mixture, the method comprising the steps of (a) introducing the aqueous sample containing particulate material and the other liquid components into a mixing chamber having a liquid inlet and outlet, a gas inlet and outlet, and containing a magnetically activated stirring member;

(b) activating the stirring member to move inside the mixing chamber and to agitate the liquid contents and form a sample mixture; and, (c) if the removal of gases from the sample mixture is desired, introducing a substantially $CO_2$-free sparge gas to a lower portion of the mixing chamber simultaneously with activation of the stirring member.

79. The method of paragraph 78 wherein the other liquid components are selected from oxidizing reagent, acid and diluting water.

80. The method of paragraph 78 wherein the stirring member is activated by passing a series of current pulses through an annularly disposed solenoid coil surrounding the mixing chamber.

81. The method of paragraph 78 wherein the sparge gas is introduced into the mixing chamber through a porous gas disperser.

82. The method of paragraph 81 wherein the porous gas disperser has pores with a pore diameter of about 1 μm to 0.125 in.

83. The method of paragraph 79 wherein step (c) is carried out for a period of about 10 seconds to 20 minutes at a sparge gas flow rate of about 50 to 500 cc/min.

84. A method for measuring a chemical component of a fluid stream comprising the steps of:

(a) providing a non-dispersive infrared (NDIR) detector apparatus comprising:

(i) a sealed IR source chamber comprising an IR source chamber purge gas inlet and a purge gas outlet, and containing an infrared radiation source;

(ii) a sealed IR detector chamber comprising an IR detector chamber purge gas inlet and a purge gas outlet, and containing an infrared detector; and, (iii) between the IR source chamber and the IR detector chamber, a sealed optical path chamber having an optical chamber fluid inlet port at a first end of the optical path chamber and an optical chamber fluid outlet port at a second end of the optical path chamber;

(b) flowing a fluid stream containing the chemical component into the inlet port, through the optical chamber, and out through the outlet port, while IR radiation is being directed through the optical chamber;

(c) throughout step (b), flowing a purge gas that is substantially free of the chemical component being measured through the IR source chamber and the IR detector chamber;

(d) modulating the intensity of the IR radiation directed through the optical chamber; and, (e) based on the detection response of the chemical detector to the passage of the fluid stream through the optical chamber, calculating a concentration of the chemical component using a mathematical correlation formula.

85. The method of paragraph 84 wherein the NDIR includes an optical filter that filters IR radiation at wavelengths other than the wavelength that is absorbed by the chemical component.

86. The method of paragraph 85 wherein the chemical component is $CO_2$ and the optical filter is a 4.26 µm±0.2 µm optical filter.

87. The method of paragraph 84 wherein step (e) is based either on a determination of peak absorbance of the IR radiation by the chemical component in the fluid stream flowing through the optical chamber or by determining the area of the complete response curve generated by passing the fluid stream through the optical chamber.

88. The method of paragraph 84 further comprising the steps of automating the NDIR detection and measurement sequence with an electronic/computer control system comprising:
   (a) a driver to actuate the IR source at the modulation frequency;
   (b) a bandpass filter to pass the infrared detector signal content at the modulation frequency, while rejecting DC offset, noise, and harmonics of the modulation frequency;
   (c) an analog-to-digital converter to sample the output of the bandpass filter many times during each modulation cycle; and,
   (d) digital signal processing elements to further bandpass filter the samples from the analog-to-digital converter to reject noise while passing the signal at the modulation frequency, and to calculate the amplitude of the resulting AC signal.

89. The method of paragraph 84 further comprising the steps of automating the NDIR detection and measurement sequence with an electronic/computer control system.

90. A method for introducing measured volumes of an aqueous sample and one or more other liquids into an analytical instrument using a single measurement syringe without contaminating the syringe with the sample or the other liquids, said method comprising the steps of:
   (a) providing a sample/reagent handling system comprising:
      (i) separate sources of one or more liquids selected from an aqueous solution/suspension, dilution water, and one or more reagents;
      (ii) conduit connections between the sources of the aqueous solution/suspension and the reagents and a first end of a length of holding tubing, and a dilution water conduit connection between the dilution water source and a second end of the tubing;
      (iii) a calibrated syringe in fluid communication with the dilution water conduit connection, the syringe having an internal volume that is less than or equal to the internal volume of the tubing; and,
      (iv) fluid valves along each of the conduit connections;
   (b) filling the holding tubing with dilution water;
   (c) drawing a first measured volume of a first one of the aqueous sample or the other liquids into the first end of the tubing by opening and/or closing the appropriate fluid valves and then opening the syringe to draw the first measured volume of dilution water into the syringe from the second end of the tubing;
   (d) drawing a second measured volume of a second one of the aqueous sample or the other liquids into the first end of the tubing by opening and/or closing the appropriate fluid valves and then additionally opening the syringe to draw the second measured volume of dilution water into the syringe from the second end of the tubing; and,
   (e) transferring the first measured volume of the first one of the liquids and the second measured volume of the second one of the liquids to a mixing location by opening and/or closing the appropriate fluid valves and then closing the syringe to fully discharge all of the dilution water in the syringe back into the second end of the tubing thereby driving the liquids in the first end of the tubing out of the tubing.

91. The method of paragraph 90 further comprising the step between steps (d) and (e) of drawing a third measured volume of a third one of the aqueous sample or the other liquids into the first end of the tubing by opening and/or closing the appropriate fluid valves and then additionally opening the syringe to draw the third measured volume of dilution water into the syringe from the second end of the tubing.

92. The method of paragraph 90 wherein the holding tubing is coiled to occupy a smaller space.

93. The method of paragraph 90 further wherein the sample/reagent handling system includes a multi-way fluid hub located along the conduit connections between the liquid sources and the first end of the tubing.

94. An analytical method comprising the steps of:
   (a) introducing measured volumes of an aqueous sample and one or more other liquids into an analytical apparatus according to the method of paragraph 90;
   (b) transferring the measured volumes of liquids from the first end of the holding tube to a mixing location where the liquids are thoroughly mixed and, optionally, can also be sparged to form a sample mixture;
   (c) flowing at least a portion of the sample mixture to a sealable reaction vessel, and treating the sample mixture by the steps of
      (i) sealing the portion of sample mixture in the interior of the reaction vessel;
      (ii) rapidly heating the interior of the reaction vessel and the sample mixture portion inside to temperature and pressure substantially above ambient conditions and for a time sufficient substantially to oxidize the organic material and form a reactor product;
      (iii) stopping the heating step and then rapidly cooling the interior of the reaction vessel and the reactor product inside to substantially ambient conditions to form cooled liquid and gaseous reactor products; and,
      (iv) opening the reaction vessel and removing the cooled liquid and gaseous reactor products from the reactor interior; and,
   (d) transferring at least the gaseous reactor product to a chemical detector and measuring a chemical component of the gaseous reactor product using the detector.

95. The method of paragraph 94 further including the step of treating the reactor product in a gas/liquid separator to remove the liquid reactor product before sending the gaseous reactor product to the chemical detector.

96. The method of paragraph 94 further wherein the chemical detector is a non-dispersive infrared (NDIR) detector.

These and other specific method and apparatus embodiments of this invention will be better understood in connection with the following detailed invention description and the several drawings in which:

DETAILED DESCRIPTION OF PREFERRED EMBODIMENTS

Figure 1:
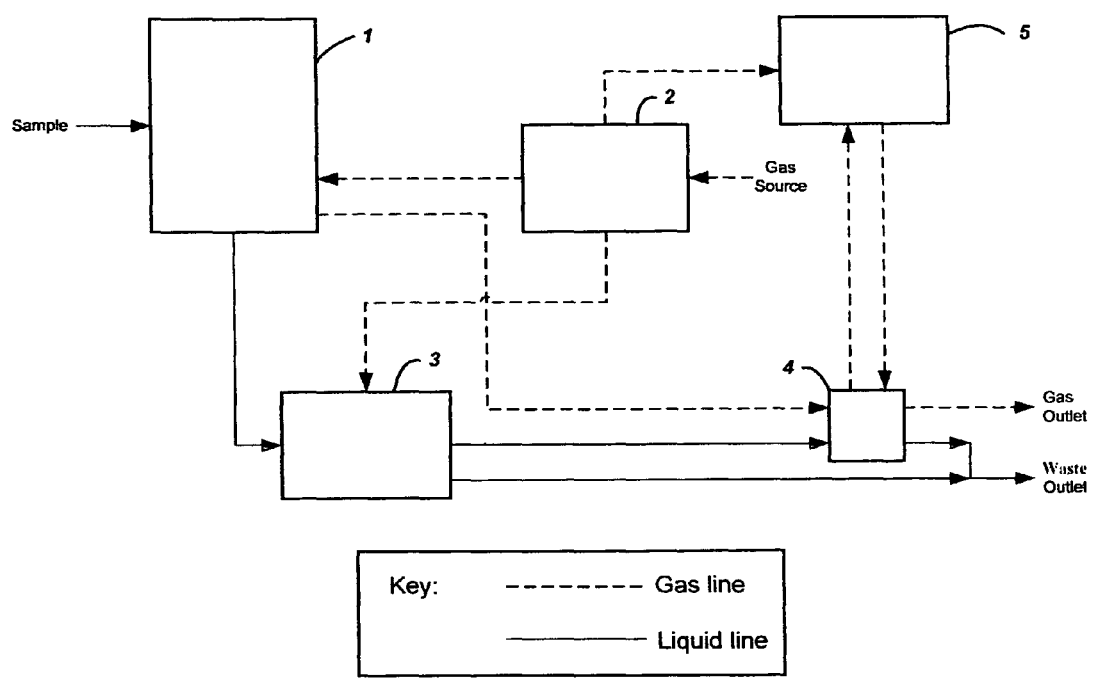
FIG. 1 (Block Diagram) is a diagram showing in block form the five key fluidic sub-assemblies of a preferred embodiment of a measurement apparatus according to this invention.

FIG. 1 is a block schematic of one preferred embodiment of an automated carbon measurement apparatus/analyzer according to this invention illustrating the five component sub-assemblies 1 to 5 that comprise the analyzer. As illustrated in FIG. 1, an aqueous sample is drawn into a sample-handling sub-assembly 1 of the apparatus, where the desired volumes of acid reagent and/or oxidizer reagent are added to a selected volume of sample. The sample may also be diluted at this stage with low-TOC dilution water if necessary before being passed to reactor sub-assembly 3.

The sample, reagents and dilution water if any are mixed in the sample-handling portions of the apparatus to create a sample mixture comprising a substantially homogenous solution or suspension. If NPOC is to be measured, the acidified sample mixture also is sparged with $CO_2$-free gas provided by the gas control sub-assembly/module 2. The flow rate of the sparge gas is controlled to ensure that IC in the sample is removed efficiently and substantially completely. If TC or IC is to be measured, the sample mixture is mixed but not sparged.

A portion of the homogenous solution/suspension is then transferred to the reactor sub-assembly 3. If NPOC or TC is to be measured, the solution/suspension containing oxidizer is heated in a sealed reactor to oxidize the organic compounds in the solution/suspension, and then it is cooled to near room temperature. If IC is to be measured, oxidizer is not added to the solution/suspension. In this case, the solution/suspension may be warmed to facilitate conversion of bicarbonates and carbonates to $CO_2$, but it is not heated so much that oxidation of organic compounds occurs.

Next, a stream of carrier gas from the gas control assembly/module 2 transfers the liquid and gas products in the reactor sub-assembly 3 to a gas/liquid separator sub-assembly/module 4. The liquid exits the analyzer from the gas/liquid separator module 4 while the gas product, containing the $CO_2$, flows to the NDIR detector sub-assembly 5. After the $CO_2$ in the gas product is measured, the gas product and carrier gas mixture can be flowed through the gas/liquid separator module 4, and vented to the atmosphere.

Figure 2:
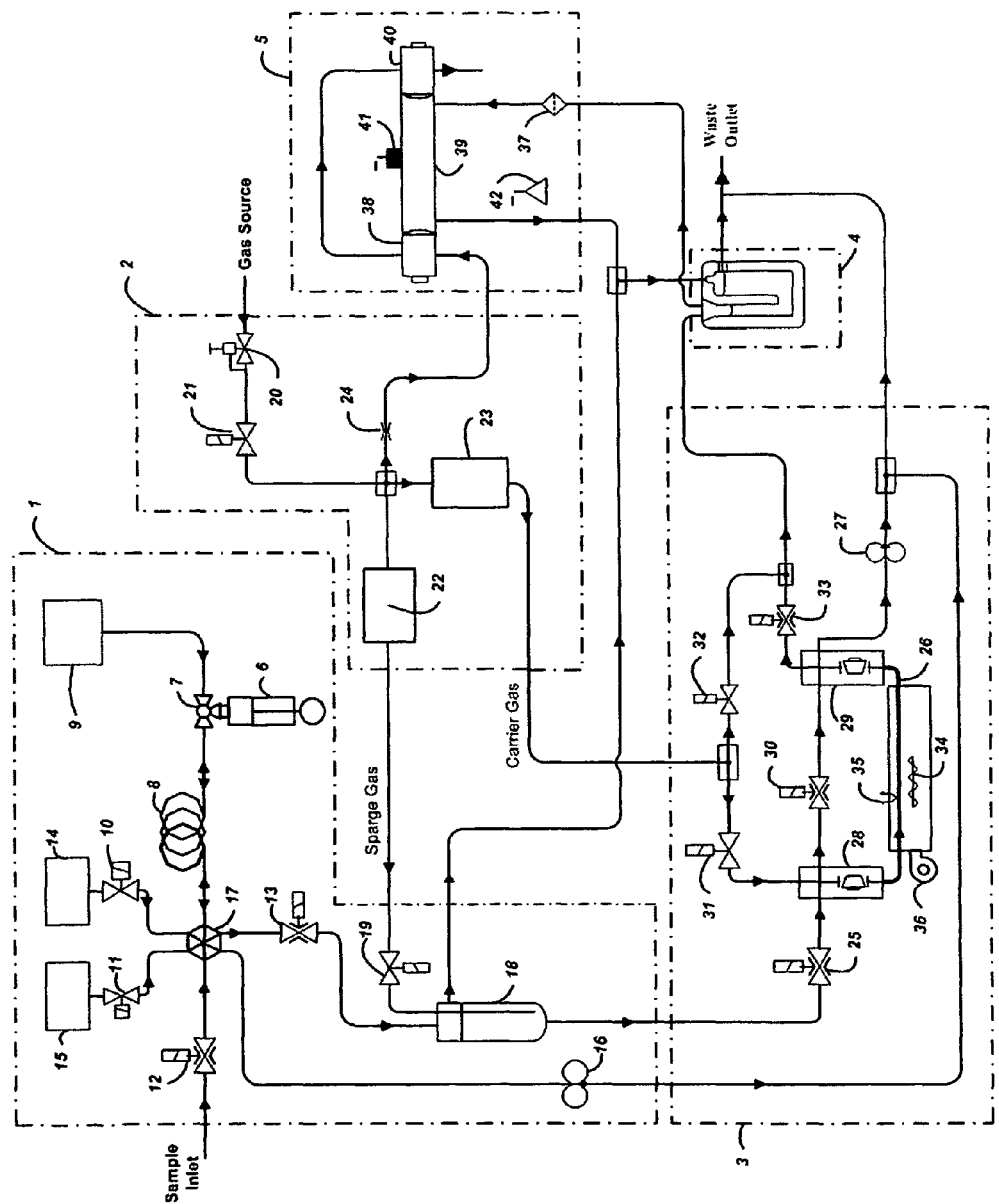
FIG. 2 (Fluidics Schematic) is an overall schematic of the functional components of a measurement apparatus according to this invention showing in detail the several component elements that comprise each of the several fluidic sub-assemblies as illustrated in FIG. 1.

FIG. 2 is a schematic showing the several fluidic components of the apparatus in more detail. In FIG. 2, sub-assemblies 1 to 5 as shown in FIG. 1 are delineated by broken lines. The sample-handling sub-assembly 1 comprises a syringe 6 that is connected through a three-way valve 7 to a coil of tubing 8 and a dilution water reservoir 9 containing low-TOC dilution water. A representative practice of the invention using the apparatus as illustrated in FIG. 2 is described below. It will be understood, however, that alternative sequences and methods for introducing the sample, reagent(s) and dilution water into the system could be used consistent with the scope of this invention. For example, using the apparatus illustrated in FIG. 2, the oxidizer and acid reagents could be moved from coil 8 to a mixing location in the apparatus, such as to mixer/sparger 18, prior to introducing the sample into the system in order to maintain a separation between these components until they are ready to be mixed at the mixing location.

Initially, the syringe is empty, and the valve 7 and coil 8 contain only dilution water. The volume of coil 8 is designed and selected to be at least as large as, and preferably larger than, the volume of syringe 6, so the only liquid that can enter the syringe is dilution water from coil 8 or reservoir 9. When an analysis begins, valve 10 is open, and valves 11, 12, and 13 are closed. Syringe 6 starts filling with dilution water drawn from a syringe end of coil 8, which causes oxidizer reagent from oxidizer reagent reservoir 14 to be drawn through the six-way fluid element 17 and into a sample/reagent end of coil 8. When syringe 6 has drawn the required volume of oxidizer into the sample/reagent end of coil 8, syringe 6 stops momentarily and valve 10 closes. Valve 11 opens and syringe 6 draws additional dilution water from the y syringe end of coil 8 into syringe 6, which in turn draws the required volume of acid from acid reservoir 15 into the sample/reagent end of coil 8, where it may partially mix with the oxidizer reagent already in this end of coil 8. When the desired volume of acid has entered coil 8, the syringe 6 stops momentarily, valve 11 closes, and valve 12 opens to allow the required volume of sample to be drawn into the sample/reagent end of coil 8, as additional dilution water from the syringe end of coil 8 is drawn into syringe 6. When the required volume of sample has entered the coil, syringe 6 stops again, and valve 12 closes. The coil 8 now contains the desired volumes of oxidizer, acid, and sample solution required for the measurement. Coil 8 may or may not contain a material amount of dilution water at this point, depending on the internal volume of coil 8 relative to the volumes of oxidizer, acid and sample drawn into coil 8, and also depending upon whether or not the sample requires dilution prior to analysis.

It will be understood that, if the procedure described above took any significant amount of time to complete, there would be an opportunity for oxidizer reagent or, perhaps, even acid, from the sample/reagent end of coil 8 to diffuse into dilution water at the syringe end of coil 8, which could lead to contamination of the syringe. In practice, however, the several steps of filling coil 8 are completed in a sufficiently short time that there is no opportunity for reagents drawn into the sample/reagent end of coil 8 to diffuse into the dilution water at the syringe end of coil 8.

In some cases, the source of the sample is a long distance from the analyzer, especially when the analyzer of this invention is used to monitor a process stream of an industrial operation. In such a situation, the analyzer could not provide real-time measurements if the only way of pumping the sample to the analyzer were the syringe pump. Therefore, in a preferred embodiment of the invention, the apparatus also includes a pump 16 which can rapidly draw a fresh portion of sample to the six-way union 17. Once the new sample portion has been delivered to element 17, it can be drawn into coil 8 quickly by further opening syringe 6 at the appropriate time.

The next step in the measurement method is to open valve 13. With valve 13 open, the step of closing syringe 6 results in moving the liquids from coil 8 to a mixing location in the system, such as to the mixer/sparger component 18, where the reagents, sample, and dilution water, if any, are thoroughly mixed. Particulate material in the sample is kept in suspension so that the solution/suspension is substantially homogeneous.

In one alternative and sometimes preferred embodiment, the acid and oxidizer are first drawn into coil 8 and then are transferred into mixing/sparging chamber 18. The sample and dilution water (if any) are then drawn into coil 8 and transferred into mixing/sparging chamber 18 where the sample, acid, oxidizer, and dilution water are mixed. Transferring the liquids to the mixing/sparging chamber 18 in two steps has the advantage of preventing premature reaction of IC in the sample with the acidic reagents in coil 8. Generation of gas in coil 8 (from reaction of IC in the sample with acid) reduces the volume of sample drawn into coil 8, adversely affecting the accuracy of the measurement.

Mixer/sparger 18 includes a mixing and sparging chamber that also is designed to provide for sparging $CO_2$-free gas through the solution/suspension to remove IC, if NPOC is to be measured. For sparging, after the chamber element of mixer/sparger 18 contains the reagents, sample and dilution water (if any), valve 19 opens to allow the sparge gas to bubble through the chamber element of mixer/sparger 18. The gas can be provided from a pressurized gas cylinder (not shown) or from a pump (not shown) that draws ambient air through an absorber that purifies the air sufficiently for use as a $CO_2$-free sparge gas, and/or as a carrier gas, and/or as a purge gas. In either case, the $CO_2$-free gas is prepared for use in gas control sub-assembly module 2. Sub-assembly 2 includes a pressure-regulating device 20 that adjusts the pressure of the gas to about 20 psig. A proportioning valve 21 controls the flow rate of the gas flowing through valve 19 by means of a sparge gas flow sensor 22. Additionally, a carrier gas flow sensor 23 in another conduit branch can be used to monitor and control the flow rate of the carrier gas to reactor sub-assembly 3. Additionally, a restrictor 24 in still another conduit branch can be used to provide for a small flow rate of purge gas to the NDIR detector.

In an alternative embodiment, a valve (not shown) can be used to direct the gas that exits the chamber element of mixer/sparger 18 through the gas/liquid separator unit 4 and then to the NDIR sub-assembly 5. This arrangement would allow the completeness of the sparging process to be monitored. Thus, the sparging is considered complete when the NDIR indicates that the concentration of $CO_2$ in the sparge gas going to the NDIR has decreased to a very small (negligible) value.

When the sparging and/or mixing in the chamber element of mixer/sparger 18 is complete, valve 25 opens to allow all or a portion of the solution/suspension in the chamber element to be drawn into the interior of reactor 26 by pump 27. High-pressure reactor inlet and outlet valves 28 and 29 respectively are open at this point. Valves 30, 31, 32, and 33 are closed. The reactor heater 34 is off, and reactor 26 is near ambient temperature. Pump 27 operates until sufficient liquid from chamber 18 has passed through the interior of reactor 26 substantially to rinse out any remaining prior sample and to fill the reactor tube inside reactor 26. At this point, pump 27 is stopped, and valves 25, 28, and 29 close.

Reactor valves 28 and 29 are specially designed in accordance with this invention to allow the valve housings to be flushed after these valves are closed. The flushing step removes excess sample that contains $CO_2$ formed by the acidification of the IC in the sample. If this $CO_2$ were not flushed out of the valves, it would cause an error in the subsequent measurement. To flush the reactor valve housings, valves 30 and 31 are opened, and residual liquid and gases in these housings can then be pumped out by pump 27 and replaced by carrier gas.

After the reactor tube of reactor 26 has been filled with sample and reactor valves 28 and 29 have been flushed, valve 31 closes and valve 32 opens to allow carrier gas to flow from sub-assembly 3 through valve 32, pass through the gas/liquid separator 4, and then pass to the NDIR detector sub-assembly 5. Flow of carrier gas at this time is necessary to allow the NDIR detector to reach a steady baseline prior to the subsequent $CO_2$ measurement. An in-line filter 37 may be provided between gas/liquid separator 4 and the NDIR unit to prevent aerosols from the reactor 26 and/or from gas/liquid separator 4 from entering the optical path 39 of the NDIR detector.

To measure NPOC or TC, the organics contained in the sample portion in the reactor tube of reactor 26 must be oxidized. This oxidation can be made to occur by heating the interior of reactor 26 with a heater 34, while controlling the temperature using a temperature sensor 35. The sealed reactor can be heated, for example, to a temperature between about 150° C. and 650° C. (preferably between about 300° C. and 400° C., and between about 350° C. and 390° C. in one preferred embodiment). The heating period may be between about one to thirty minutes, preferably between about two and four minutes, and approximately 3 minutes in one preferred embodiment. During this period, organics are oxidized in the sample portion in the reactor. At the end of that period, heating element 34 is turned off, and fan unit 36 is turned on to blow ambient air over reactor 26, cooling it rapidly to near room temperature. Because of the small mass of reactor 26, it is typically cooled by this cooling step to near ambient temperature in less than about 90 seconds.

To measure IC, the liquid inside reactor 26 is not oxidized. The reactor is filled as described above, but reactor 26 is heated only to a temperature sufficient to facilitate formation of $CO_2$ from bicarbonates and carbonates (i.e., typically to no more than about 100° C.). The subsequent cooling step may in this case be abbreviated or omitted entirely. Furthermore, the oxidizer reagent is not required for IC measurements, and its addition to the sample prior to the reactor step can thus be omitted to reduce operating cost and make the analysis faster.

When the heating and cooling of reactor 26 is completed (or the comparable IC reactor sequence is completed), valves 30 and 32 close, and valves 28, 29, 31, and 33 open. This apparatus configuration allows carrier gas to flow through the reactor tube of reactor 26, and carry the reactor products through gas/liquid separator 4, to the NDIR sub-assembly and along the NDIR optical path 39.

The NDIR measures the absorbance of the $CO_2$ in the gas flowing along NDIR optical path 39 at a wavelength of approximately 4.26 μm, e.g., 4.26 μm±0.2 μm. As the $CO_2$ carried from reactor 26 enters and passes through the NDIR, the absorbance measurement begins at a baseline level, rises up to and passes through a maximum level, and then returns to the baseline level that existed before the valves associated with reactor 26 opened. Either the height of the absorbance peak (or the depth of the intensity trough) or the cone-shaped area of the absorbance response curve can be calibrated and used to determine the amount of $CO_2$ contained in the gas product coming from the reactor.

Figure 6:
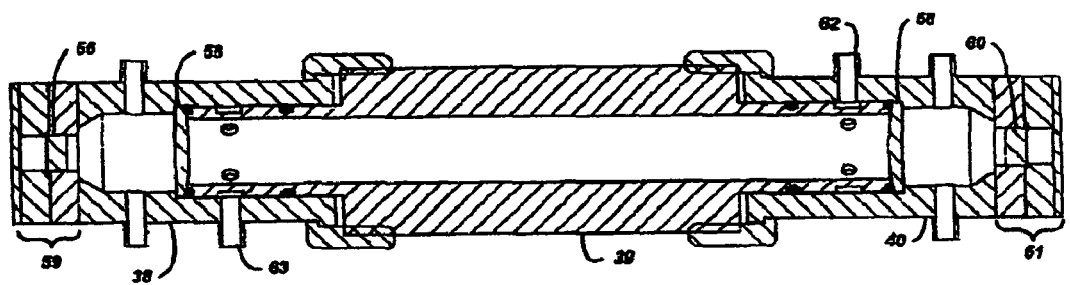
FIG. 6 (NDIR Optical Bench) is a schematic, partially cut-away/sectional view of an NDIR sub-assembly in accordance with this invention.

The NDIR detector of this invention is comprised of three chambers, as seen in FIGS. 2 and 6. One chamber 38 contains the IR source. The central chamber, which is the NDIR optical path 39, is the chamber through which the carrier gas and the gas product from reactor 26 (which includes the $CO_2$) flow. The third chamber 40 contains the IR detector. Chambers 38 and 40 are flushed by $CO_2$-free gas provided through the conduit that includes flow controller 24 so that $CO_2$ in the ambient air does not affect the measurements made with the NDIR. The NDIR further preferably includes an associated temperature sensor 41 and an associated pressure sensor 42, proximately located relative to the NDIR, which monitors atmospheric pressure outside the NDIR (which is essentially the same as the pressure of the $CO_2$ in the NDIR). The temperature and pressure measurements made respectively by temperature sensor 41 and pressure sensor 42 can be used to compensate the response of the NDIR for variations in the temperature and pressure of the gas being measured. Alternatively, sensors 41 and/or 42 may be omitted if the measurement does not require temperature and/or pressure compensation.

Figure 3:
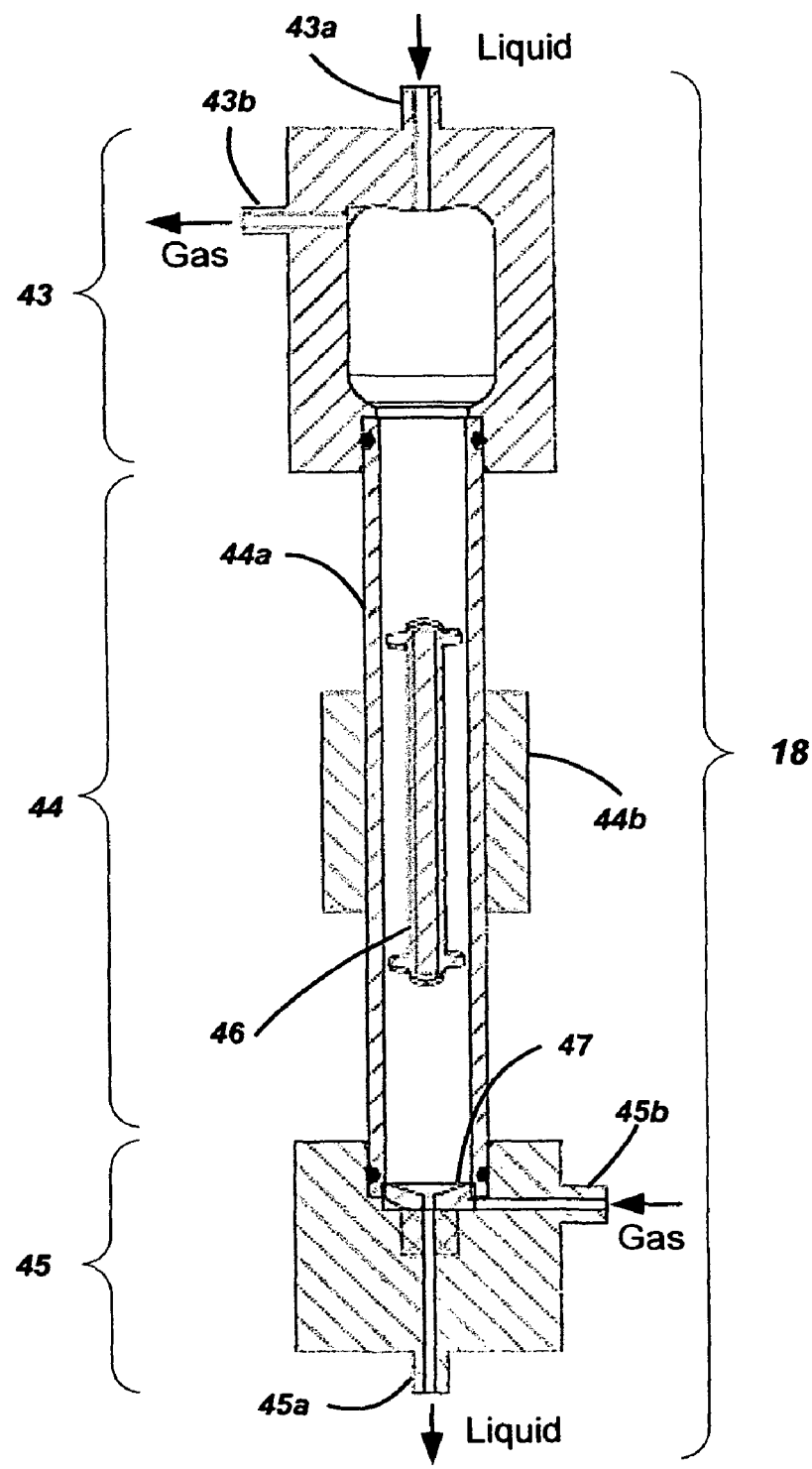
FIG. 3 (Sparger With Mixing Function) is a schematic, partially cut-away/sectional view of a mixer/sparger component in accordance with this invention.

One of the several novel components of the apparatus of this invention is the mixer/sparger 18. As shown in greater detail in FIG. 3, the preferred mixer/sparger of this invention includes a liquid inlet/gas outlet section 43, a middle section 44, and a liquid outlet/gas inlet section 45. The top section 43 contains a liquid inlet 43a and the sparge gas outlet 43b. The bottom section 45 includes the inlet port 45b for the sparge gas and the outlet 45a for liquid. The middle section 44 includes a chamber element 44a located inside an annular solenoid coil 44b, which is activated by passing a series of current pulses through it. Such current waveform pulsing causes a magnetic stirrer 46 positioned inside chamber 44a to rapidly move up and down inside chamber 44a. In a preferred embodiment, the magnetic stirrer 46 is coated with a corrosion-resistant outer layer, and its up-and-down action under the influence of the solenoid-generated waveform pulses causes the sample, reagents and dilution water, if any, inside chamber 44a to be rapidly mixed, typically in about 60 seconds or less.

The bottom section 45 of mixer/sparger 18 includes a porous gas disperser 47, through which sparge gas is directed on its way into chamber 44a. The pore diameter in the gas disperser 47 may be about 1 μm to 0.125 in., e.g., preferably about 5 μan to 50 μm, and about 18 μm in a preferred embodiment. The small bubbles produced by passing the sparge gas through disperser 47 results in efficient removal of IC from the liquid in chamber 44a, generally in about 10 seconds to 20 minutes at sparge gas flow rates ranging from about 50 to about 500 cc/min., typically and preferably in about one minute or less at a sparge gas flow rate of about 200 cc/min.

Figure 4:
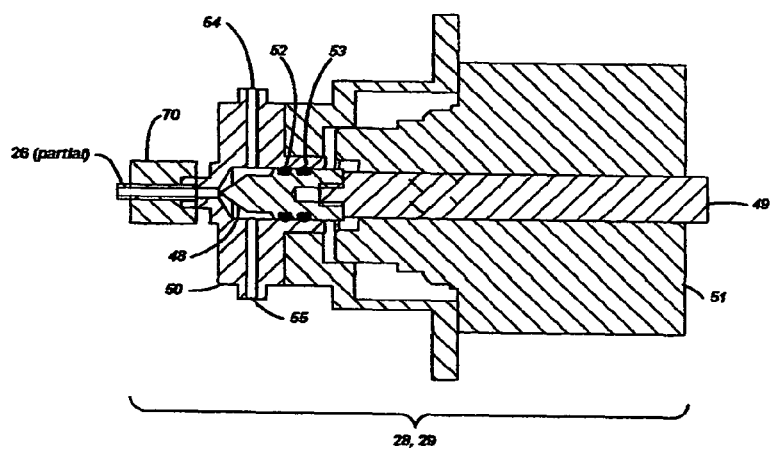
FIG. 4 (High-Pressure Valve) is a schematic, partially cut-away/sectional view of a high-pressure reactor valve used to seal the reactor in accordance with this invention.

Another of the novel components of the apparatus of this invention are the high-pressure reactor valves 28 and 29 as shown in FIG. 2, and as illustrated in greater detail in FIG. 4. These high-pressure reactor valves are included in a preferred embodiment of the present invention. As seen in FIG. 4, a polymeric or elastic seal 48 is attached to or comprises a front end or section of a moveable plunger element 49, which is designed to move back and forth inside the housing/valve body 50 when motor 51 is activated. The rear portion of seal 48 is adapted to retain first and second O-rings 52 and 53 respectively, which seal the interior of housing 50. The front end of seal 48 is sized and shaped to mate with and plug an opening (i.e., an inlet opening or an outlet opening) of reactor 26 when the valve is closed by advancing plunger element 49. Reactor 26 may be attached to valve housings 50, for example, using fittings 70 (as seen in FIG. 4), which provide a seal that is essentially leak-free at the pressure produced in reactor 26 when the solution/suspension is sealed inside reactor 26, and reactor 26 is heated.

Seal 48 is enclosed by a seal chamber defined by the valve housing 50 extending from the sealed opening of reactor 26 at least to first O-ring 52. This chamber can be continuously or periodically flushed with gas using seal chamber ports 54 and 55 as shown in FIG. 4. (Reactor valves 28 and 29 also each have a third port that is not seen in FIG. 4. The sample solution/suspension enters or exits the valve and the interior of reactor 26 through that third port.) This apparatus configuration makes it possible to remove any IC or free $CO_2$ that may be present in the valve housing 50 while the sample is being oxidized/treated in reactor 26.

Figure 5:
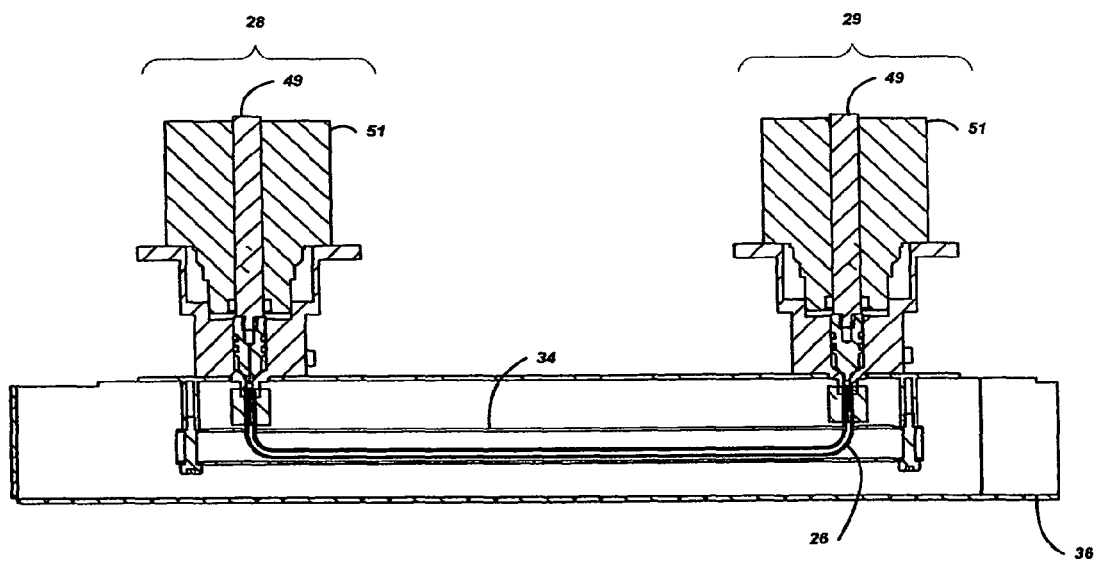
FIG. 5 (Reactor Assembly) is a schematic, partially cut-away/sectional view of a reactor sub-assembly in accordance with this invention.

FIG. 5 is a schematic illustration of reactor valves 28 and 29 mounted at either end of a reactor 26. In a preferred embodiment, the reactor heater element 34 has a tubular configuration open at both ends and located inside a heater housing with the reactor 26 mounted inside the tubular portion of heater 34. In a preferred embodiment, heater 34 comprises a thick-film heating element deposited on an electrically insulating coating on the tubular portion of heater 34, as shown in FIG. 5. The tubular portion of heater 34 may be constructed of stainless steel, titanium, or other suitable materials. The two ends of reactor 26 pass respectively through slots (not shown in FIG. 5) in the sidewall of the tubular portion of heater 34. In a preferred embodiment, reactor 26 is a tube constructed of titanium; however, stainless steel, ceramics, and other materials that are sufficiently corrosion-resistant and compatible with the oxidation temperatures of this invention can be used. As previously discussed, the reactor assembly preferably also includes a fan component to cool the reactor after a heating/oxidation step. As seen in FIG. 5, the outlet (downstream side) of fan 36 is preferably positioned close to one open end of the heater 34, and is oriented so that a flow of cooling air during a cooling step passes through the heater housing and over both the exterior and interior of heater 34, and also such that the airflow going through the interior of the tubular portion of the heater 34 during a cooling step passes over the portion of reactor 26 contained within the tubular portion of heater 34.

The special NDIR detector sub-assembly 5 of this invention is shown in greater detail in FIG. 6. The NDIR consists of an optical system and an associated NDIR electronic system (as illustrated in the block diagram of FIG. 7). The NDIR optical system has three major sections: an IR source compartment 38, a sample cell/NDIR optical path 39, and an IR detector compartment 40. Collimating lenses 58 located at either end of sample cell 39 separate the adjacent sections. In a preferred embodiment, the lenses 58 are constructed of silicon.

In a preferred embodiment, the IR source 56 is a thin-film heater. It may be mounted in plates 59 that are attached to an IR source heater and an IR source temperature sensor. Using the associated NDIR electronic system, the plates 59 and IR source 56 are controlled to a temperature of about 65° C. in one preferred embodiment.

In a preferred embodiment, the IR detector 60 is a pyroelectric, lithium tantalate sensor element. A 4.26 μm filter is mounted in the IR detector in front of the sensor element. This filter selectively passes infrared radiation at the wavelength that is absorbed by $CO_2$. Thus, the IR detector 60 measures the IR radiation that passes through the optical path 39 and the filter without being absorbed by $CO_2$.

The IR detector 60 may be mounted in plates 61 attached to an IR detector heater and an IR detector temperature sensor. In a preferred embodiment, the IR detector 60 is controlled at a temperature of about 55° C. using the associated NDIR electronic system.

Carrier gas and the gas product from reactor 26, including the $CO_2$, flow through the center section 39 of the NDIR. IR source 56 and IR detector 60, located in their separate compartments, are isolated from water vapor and potentially corrosive oxidation products by the compartment separation lenses 58. The chambers 38 and 40 are also sealed, and $CO_2$ from ambient air is prevented from entering, or at least from remaining in, those chambers by flowing purge gas provided by the gas control sub-assembly 2. The center section 39 of the NDIR has a gas inlet port 62 and a gas outlet port 63, through which the carrier gas and the gas product from the reactor, including the $CO_2$, flow. As illustrated in FIG. 6, the gas inlet port 62 may be located proximate to the IR detector end of the NDIR, while the gas outlet port 63 is located proximate to the IR source end of the NDIR. However, the reverse orientation also is effective.

Figure 7:
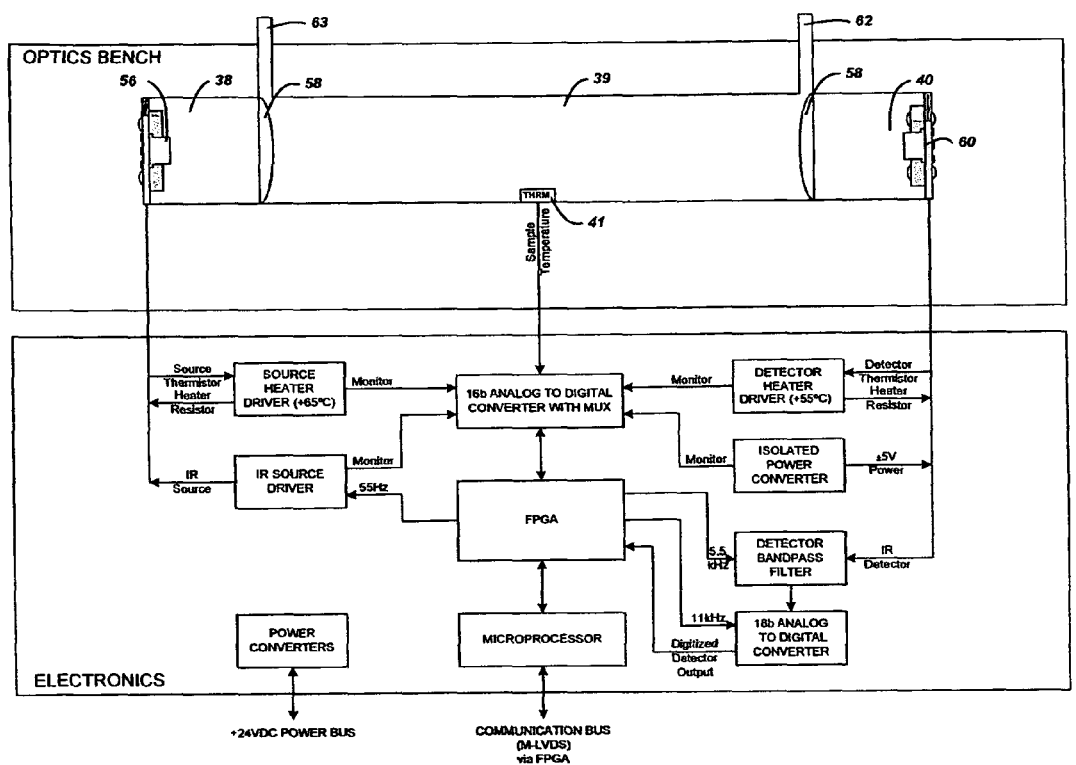
FIG. 7 (Block Diagram of NDIR Detector) is a block diagram illustrating internal details and related electrical connections and components of an NDIR sub-assembly as illustrated in FIG. 6.

The electronic system for operating the NDIR sub-assembly in a preferred invention embodiment is schematically illustrated in FIG. 7. As seen in FIG. 7, the electronic system includes electronic devices selected to provide power to the IR source, the IR source heater, the IR detector, the IR detector heater, and other electrical components. In a preferred embodiment, the electronics control system modulates the power to the IR source at a frequency of 55 Hz. Signals may be generated at other frequencies for operation of other components, such as the bandpass filter and analog-to-digital converter, from a field-programmable gate array (FPGA) as is known in the art.

The FPGA can be adapted or adjusted to generate a 55 Hz clock for the IR source, with a duty cycle suitable for its operation. The IR source driver converts the logic-level clock signal into the pulsed power required by the IR source. The IR source emits infrared light, modulated at 55 Hz. This light reaches the IR detector, attenuated by any $CO_2$ present in the center section 39 of the NDIR. The IR detector converts the infrared light that it receives back into an electrical signal, with signal content at 55 Hz that is proportional to the infrared light that it receives. The detector bandpass filter is selected or adapted to remove harmonics of the 55 Hz signal and DC offset, low-frequency noise, and high-frequency noise generated by the IR detector. A synchronous circuit, such as a switched-capacitor filter, is used in the detector bandpass filter, with a clock provided by the FPGA at a multiple of 55 Hz. The analog-to-digital converter samples the waveform from the detector bandpass filter, also using a clock provided by the FPGA at a whole number multiple of 55 Hz. For example, a clock of 5500 Hz provides 100 waveform samples per cycle of the IR detector waveform. The FPGA and the microprocessor perform further bandpass filtering of the digitized IR detector signal, centered at the modulation frequency of 55 Hz, to remove detector noise and noise from the AC mains at 50 Hz or 60 Hz. The amplitude of the 55 Hz signal at the output of the digital bandpass filter is then measured. The response of the IR detector is adjusted for temperature, pressure, and flow rate as necessary, and the $CO_2$ concentration is calculated in the manner described above. Based on the description provided herein, the processing steps described above could readily be implemented by one of ordinary skill in this art using an apparatus in accordance with this invention.

Figure 8:
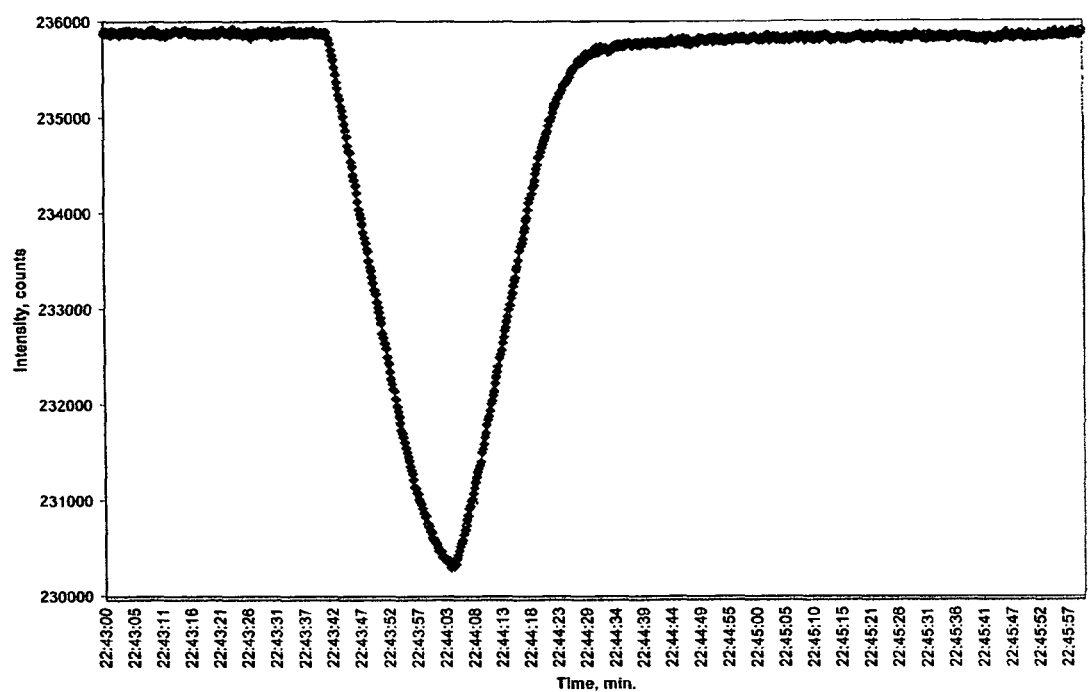
FIG. 8 (Response to $CO_2$) is a graph illustrating a typical response of a NDIR detector in accordance with this invention to $CO_2$ contained in a gaseous reactor product produced in the instrument by oxidation of organic compounds.

FIG. 8 illustrates a typical response curve of an NDIR during a carbon measurement sequence. The output is in instrument counts, and the counts are proportional to the amount of IR radiation that strikes the IR detector 60. When there is no $CO_2$ in section 39, the response is at its maximum or baseline level. As soon as $CO_2$ enters section 39, the response decreases until it reaches a minimum (trough) that corresponds to when the amount of $CO_2$ in section 39 has reached its maximum (maximum absorbance). As the $CO_2$ passes out of section 39, the response returns to its original baseline level.

There are two ways that the response peak (trough) can be used to calculate carbon concentrations in an aqueous sample being tested. The response curve can be mathematically integrated, and the resulting cone-shaped area of the response curve can be related to carbon concentration by one type of mathematical calibration correlation. Alternatively, the height of the peak (depth of the trough) can be measured and related to carbon concentration by another type of mathematical calibration correlation. These mathematical calibration correlations can be developed for a particular instrument according to this invention by performing tests on samples containing known concentrations of IC, OC and/or TC. Basing computations on the measurement of peak height has the advantage that it is relatively unaffected by changes in gas flow rate; and, for that reason, this is the technique used in a preferred embodiment of the present invention.

The present invention has been described in detail with reference to preferred embodiments thereof for illustrative purposes. Although specific terms are employed in describing this invention, they are used and are to be interpreted in a generic and a descriptive sense only and not for purpose of limitation. Accordingly, it will be understood to those of ordinary skill in the art that various changes, substitutions and alterations in form and details may be made without departing from the spirit and scope of the present invention as set forth in the following claims.

The invention claimed is:

1. An analytical instrument comprising in combination: a liquid sample inlet; a fluid transport system for drawing a known volume of a liquid sample into the instrument and for transporting liquids and gases to and through the components of the instrument including a reactor downstream of the liquid sample inlet; a reactor having a reactor interior, reactor inlet and reactor outlet ports, and reactor sealing valves at the reactor inlet and the reactor outlet ports that can alternately be opened, to introduce a liquid sample to the reactor interior or to discharge a reactor product from the reactor interior, or sealed to heat treat a liquid sample inside the reactor interior to a reaction temperature of about 150° C. to about 650° C. to produce a reactor product; a reactor heating unit that can be turned on during a reactor heating cycle to heat a liquid sample sealed in the reactor interior to the reaction temperature and turned off during a reactor cooling cycle; a reactor cooling unit that can be turned on during a reactor cooling cycle and turned off during a reactor heating cycle; a source of gas and a gas flow control system in communication with the fluid transport system; and, a chemical detector downstream of the reactor to measure a chemical component of the reactor product.

2. An analytical instrument comprising: a sample-handling unit comprising multiple valves and a syringe connected through a three-way valve to both a coil of tubing and a reservoir containing low-TOC dilution water, wherein the volume of the coil is at least as large as the volume of the syringe; a pump component effective to draw a liquid sample from a sample source and deliver it by a conduit connection to a fluid interconnection element; a mixing/sparging chamber connected to the coil of tubing, said chamber including a sparging element for sparging $CO_2$-free gas through a liquid solution/suspension in the chamber; a source of compressed $CO_2$-free gas connected to the sparging element and a gas control module to control the flow and pressure of such gas; a pump component and associated conduit to transfer at least a portion of the liquid solution/suspension from the mixing/sparging chamber to a sealable reactor having reactor sealing valves at reactor inlet and reactor outlet ports that can alternately be opened or sealed; a heater and a fan associated with the reactor; a source of carrier gas connected to the reactor; a conduit downstream of the reactor carrying the reactor product sequentially through a gas/liquid separator, an in-line filter, and then to a $CO_2$ detector; and an associated automated control system comprising electrical connections and operational software adapted to operate fluid valves and other system control elements according to a predetermined sequence and/or timing or, alternatively, in accordance with feedback received from various system monitors.

3. Apparatus for treating a liquid sample containing organic material comprising:
  (a) a reactor having reactor inlet and reactor outlet ports and a reactor interior for containing a liquid sample under above-ambient temperature and pressure conditions;
  (b) high-pressure fluid reactor valve members at said reactor inlet and reactor outlet ports, said reactor valve members allowing fluid flow respectively into or out of the reactor interior when in an open-valve mode or, alternatively, capable of sealing the reactor interior when in a closed-valve mode;
  (c) a reactor heating system that is able to rapidly and cyclically heat the reactor interior and a liquid sample sealed in the reactor interior to a temperature of about 150° C. to 650° C. or higher, while the reactor interior and the reactor valve members maintain the sample under sealed conditions; and,
  (d) a reactor cooling system adapted for rapidly and cyclically cooling the reactor interior and a reactor product sealed in the reactor interior following a heating cycle.

4. The apparatus of claim 3 wherein the reactor heating system is able to heat the reactor interior and a liquid sample sealed in the reactor interior to temperature and pressure high enough to generate supercritical fluid conditions inside the reactor interior, while the reactor interior and the reactor valve members maintain the sample under sealed conditions.

5. The apparatus of claim 3 wherein each of the reactor valve members comprises a valve housing having a main fluid inlet and a main fluid outlet, a moveable valve plunger element inside the valve housing, a front portion of the valve plunger element comprising a polymeric or elastic plunger seal member having a section sized and shaped to mate with and plug the main fluid outlet when the valve plunger element is in an advanced position, and to unseal the main fluid outlet when the valve plunger element is in a retracted position.

6. The apparatus of claim 5, each valve member further comprising a motor for alternately advancing or retracting the valve plunger element.

7. The apparatus of claim 3 wherein the reactor heating system comprises a hollow tubular heating element with the reactor in the hollow interior of the heating element.

8. The apparatus of claim 7 wherein the tubular heating element is open at each end, and further wherein the reactor cooling system comprises a fan located proximate to one open end of the heating element and oriented to blow ambient air through the hollow interior of the heating element and along the exterior of the reactor.

9. The apparatus of claim 3 wherein the reactor cooling system comprises a fan located proximate to the reactor and oriented to blow ambient air along the exterior of the reactor.

10. The apparatus of claim 3 further comprising in combination: a liquid sample inlet; a fluid transport system for drawing a known volume of a liquid sample into the apparatus and for transporting liquids and gases to and through the components of the apparatus including the reactor downstream of the liquid sample inlet; a source of gas and a gas flow control system in communication with the fluid transport system; and, a chemical detector downstream of the reactor to measure a chemical component of the reactor product.

11. The apparatus of claim 10 further comprising a fluid pumping system in communication with the fluid transport system.

12. The apparatus of claim 10 further comprising one or more additional inlets selected from an acid reagent inlet, an oxidizer reagent inlet and a dilution water inlet.

13. The apparatus of claim 10 further comprising a mixing/sparging chamber upstream from the reactor where a combination of a liquid sample and one or more other liquids can be either mixed or mixed and simultaneously sparged with sparge gas.

14. The apparatus of claim 10 wherein the chemical detector comprises a detector for carbon, nitrogen or sulfur oxidation products downstream of the reactor.

15. The apparatus of claim 10 further comprising an electronic/computer automated control system.

16. The apparatus of claim 3 further comprising the following elements: (A) a sample handling system upstream of the reactor including: multiple valves and a syringe connected through a three-way valve to both a coil of tubing and a reservoir containing low-TOC dilution water, wherein the volume of the coil is at least as large as the volume of the syringe; a pump component effective to draw sample from a sample source and deliver it by a conduit connection to a fluid interconnection element; a mixing/sparging chamber connected to the coil of tubing, said chamber including a sparging element for sparging $CO_2$-free gas through a solution/suspension in the chamber; a source of compressed $CO_2$-free gas connected to the sparging element and a gas control module to control the flow and pressure of such gas; and a pump component and associated conduit to transfer at least a portion of the solution/suspension from the mixing/sparging chamber to the reactor; (B) a source of carrier gas connected to the reactor; and (C) a reactor product handling system downstream of the reactor including: a conduit carrying the reactor product sequentially through a gas/liquid separator, an in-line filter, and then to a $CO_2$ detector; and an associated automated control system comprising electrical connections and operational software adapted to operate fluid valves and other system control elements according to a predetermined sequence and/or timing or, alternatively, in accordance with feedback received from various system monitors.

17. Apparatus for treating a liquid sample containing organic material comprising:
  (a) a reactor having reactor inlet and reactor outlet ports and a reactor interior for containing a liquid sample under above-ambient temperature and pressure conditions;
  (b) high-pressure fluid reactor valve members at said reactor inlet and reactor outletports, said reactor valve members allowing fluid flow respectively into or out of the reactor interior when in an open-valve mode or, alternatively, capable of sealing the reactor interior when in a closed-valve mode, and further wherein each of the reactor valve members comprises a valve housing having a main fluid inlet and a main fluid outlet, a moveable valve plunger element inside the valve housing, a front portion of the valve plunger element comprising a polymeric or elastic plunger seal member having a section sized and shaped to mate with and plug the main fluid outlet when the valve plunger element is in an advanced position, and to unseal the main fluid outlet when the valve plunger element is in a retracted position, and also wherein each valve housing comprises a purge gas inlet and a purge gas outlet whereby a purge gas can be flowed through the interior of the valve housing while the valve plunger element is sealing the main fluid outlet;

(c) a reactor heating system that is able to rapidly and cyclically heat the reactor interior and a liquid sample sealed in the reactor interior to a temperature of about 150° C. to 650° C. or higher, while the reactor interior and the reactor valve members maintain the sample under sealed conditions; and, (d) a reactor cooling system adapted for rapidly and cyclically cooling the reactor interior and a reactor product sealed in the reactor interior following a heating cycle.

18. Apparatus for treating a liquid sample containing organic material comprising:

(a) a reactor having reactor inlet and reactor outlet ports and a reactor interior for containing a liquid sample under above-ambient temperature and pressure conditions;

(b) high-pressure fluid reactor valve members at said reactor inlet and reactor outlet ports, said reactor valve members allowing fluid flow respectively into or out of the reactor interior when in an open-valve mode or, alternatively, capable of sealing the reactor interior when in a closed-valve mode;

(c) a reactor heating system that is able to rapidly and cyclically heat the reactor interior and a liquid sample sealed in the reactor interior to a temperature of about 150° C. to 650° C. or higher, while the reactor interior and the reactor valve members maintain the sample under sealed conditions; and, (d) a reactor cooling system adapted for rapidly and cyclically cooling the reactor interior and a reactor product sealed in the reactor interior following a heating cycle;

said apparatus further comprising in combination: a liquid sample inlet; a fluid transport system for drawing a known volume of a liquid sample into the apparatus and for transporting liquids and gases to and through the components of the apparatus including the reactor downstream of the liquid sample inlet; a source of gas and a gas flow control system in communication with the fluid transport system; and, a chemical detector downstream of the reactor to measure a chemical component of the reactor product wherein the chemical detector comprises a non-dispersive infrared (NDIR) detector.

19. The apparatus of claim 18 wherein the NDIR includes an optical filter selective to the wavelength of IR radiation absorbed by the chemical component to be measured.

20. The apparatus of claim 19 wherein the optical filter is selective to carbon oxidation products.

21. The apparatus of claim 19 wherein the optical filter is selective to $CO_2$.

22. The apparatus of claim 18 further comprising a gas/liquid separator between the reactor and the NDIR detector to remove liquid from the reactor product.

23. Apparatus for treating a liquid sample containing organic material comprising:

(a) a reactor having reactor inlet and reactor outlet ports and a reactor interior for containing a liquid sample under above-ambient temperature and pressure conditions;

(b) high-pressure fluid reactor valve members at said reactor inlet and reactor outlet ports, said reactor valve members allowing fluid flow respectively into or out of the reactor interior when in an open-valve mode or, alternatively, capable of sealing the reactor interior when in a closed-valve mode;

(c) a reactor heating system that is able to rapidly and cyclically heat the reactor interior and a liquid sample sealed in the reactor interior to a temperature of about 150° C. to 650° C. or higher, while the reactor interior and the reactor valve members maintain the sample under sealed conditions; and, (d) a reactor cooling system rapidly and cyclically cooling the reactor interior and a reactor product sealed in the reactor interior following a heating cycle;

said apparatus further comprising in combination: a liquid sample inlet; a fluid transport system for drawing a known volume of a liquid sample into the apparatus and for transporting liquids and gases to and through the components of the apparatus including the reactor downstream of the liquid sample inlet; a source of gas and a gas flow control system in communication with the fluid transport system; and, a chemical detector downstream of the reactor to measure a chemical component of the reactor product; and an AC signal processing element effective for noise rejection/filtering and signal amplitude measurements.

24. Apparatus for treating a liquid sample containing organic material comprising:

(a) a reactor having reactor inlet and reactor outlet ports and a reactor interior for containing a liquid sample under above-ambient temperature and pressure conditions;

(b) high-pressure fluid reactor valve members at said reactor inlet and reactor outlet ports, said reactor valve members allowing fluid flow respectively into or out of the reactor interior when in an open-valve mode or, alternatively, capable of sealing the reactor interior when in a closed-valve mode;

(c) a reactor heating system that is able to rapidly and cyclically heat the reactor interior and a liquid sample sealed in the reactor interior to a temperature of about 150° C. to 650° C. or higher, while the reactor interior and the reactor valve members maintain the sample under sealed conditions; and, (d) a reactor cooling system adapted for rapidly and cyclically cooling the reactor interior and a reactor product sealed in the reactor interior following a heating cycle;

said apparatus further comprising a mixing system upstream of the reactor for mixing a liquid sample containing particulate material with one or more other liquid components, said mixing system comprising:

(i) a sealed tubular mixing container having a liquid inlet/gas outlet section at a first container end, said liquid inlet/gas outlet section including a sample inlet and a sparge gas outlet; a liquid outlet/gas inlet section at a second container end, said liquid outlet/gas inlet section including a sparge gas inlet and a sample outlet; and, between said liquid inlet/gas outlet section and said liquid outlet/gas inlet section, a fluid mixing region;

(ii) a magnetically activatable stirrer element inside said fluid mixing region;

(iii) an annular solenoid coil surrounding at least a portion of said fluid mixing region, said solenoid coil being activatable by a series of electric current pulses to move the stirrer element inside the fluid mixing region; and, (iv) a porous gas disperser located between the sparge gas inlet and the fluid mixing region.

25. Apparatus for treating a liquid sample containing organic material comprising:
(a) a reactor having reactor inlet and reactor outlet ports and a reactor interior for containing a liquid sample under above-ambient temperature and pressure conditions;
(b) high-pressure fluid reactor valve members at said reactor inlet and reactor outlet ports, said reactor valve members allowing fluid flow respectively into or out of the reactor interior when in an open-valve mode or, alternatively, capable of sealing the reactor interior when in a closed-valve mode;
(c) a reactor heating system that is able to rapidly and cyclically heat the reactor interior and a liquid sample sealed in the reactor interior to a temperature of about 150° C. to 650° C. or higher, while the reactor interior and the reactor valve members maintain the sample under sealed conditions; and,
(d) a reactor cooling system adapted for rapidly and cyclically cooling the reactor interior and a reactor product sealed in the reactor interior following a heating cycle; further wherein each of the reactor valve members includes a purgeable fluid sealing valve assembly comprising:
(a) (i) a valve housing having a main fluid inlet and a main fluid outlet;
(b) (ii) a moveable plunger element inside the valve housing, a front portion of the valve plunger element comprising a plunger seal member sized and shaped to be seated on and plug the main fluid outlet when the valve plunger element is in an advanced position, and to unseal the main fluid outlet when the plunger is in a retracted position; and,
(iii) the valve housing further comprising a valve purge gas inlet and a valve purge gas outlet whereby a purge gas can be flowed through the interior of the valve housing while the valve plunger element is sealing the main fluid outlet.

26. Apparatus for treating a liquid sample containing organic material comprising:
(a) a reactor having reactor inlet and reactor outlet ports and a reactor interior for containing a liquid sample under above-ambient temperature and pressure conditions;
(b) high-pressure fluid reactor valve members at said reactor inlet and reactor outlet ports, said reactor valve members allowing fluid flow respectively into or out of the reactor interior when in an open-valve mode or, alternatively, capable of sealing the reactor interior when in a closed-valve mode;
(c) a reactor heating system that is able to rapidly and cyclically heat the reactor interior and a liquid sample sealed in the reactor interior to a temperature of about 150° C. to 650° C. or higher, while the reactor interior and the reactor valve members maintain the sample under sealed conditions; and,
(d) a reactor cooling system adapted for rapidly and cyclically cooling the reactor interior and a reactor product sealed in the reactor interior following a heating cycle; said apparatus further comprising a purgeable non-dispersive infrared (NDIR) detector downstream of said reactor and in fluid communication with the reactor outlet port, said detector comprising:
(i) an IR source chamber comprising an IR source chamber purge gas inlet and a purge gas outlet, and containing an infrared radiation source;
(ii) an IR detector chamber comprising an IR detector chamber purge gas inlet and a purge gas outlet, and containing an infrared detector; and,
(iii) between the IR source chamber and the IR detector chamber, an optical path chamber having an optical chamber gas inlet port at a first end of the optical path chamber and an optical chamber gas outlet port at a second end of the optical path chamber.

27. Apparatus for treating a liquid sample containing organic material comprising:
(a) a reactor having reactor inlet and reactor outlet ports and a reactor interior for containing a liquid sample under above-ambient temperature and pressure conditions;
(b) high-pressure fluid reactor valve members at said reactor inlet and reactor outlet ports, said reactor valve members allowing fluid flow respectively into or out of the reactor interior when in an open-valve mode or, alternatively, capable of sealing the reactor interior when in a closed-valve mode;
(c) a reactor heating system that is able to rapidly and cyclically heat the reactor interior and a liquid sample sealed in the reactor interior to a temperature of about 150° C. to 650° C. or higher, while the reactor interior and the reactor valve members maintain the sample under sealed conditions; and,
(d) a reactor cooling system adapted for rapidly and cyclically cooling the reactor interior and a reactor product sealed in the reactor interior following a heating cycle; said apparatus further comprising a sample/reagent handling system upstream of said reactor comprising:
(i) separate sources of one or more liquids selected from an aqueous solution/suspension containing at least an impurity, dilution water, oxidizing reagent, and acid;
(ii) conduit connections between the sources of the aqueous solution/suspension, oxidizing reagent and acid and a first end of a length of holding tubing, and a dilution water conduit connection between the dilution water source and a second end of the tubing;
(iii) a calibrated syringe in fluid communication with the dilution water conduit connection, the syringe having an internal volume that is equal to or less than the internal volume of the tubing;
(iv) a conduit connection between the first end of the tubing and a mixing device;
(v) fluid valves along each of the conduit connections such that the syringe can be used to separately draw measured volumes of oxidizing reagent, acid and aqueous solution/suspension into the first end of the tubing by drawing dilution water from the second end of the tubing into the syringe, followed by discharging the dilution water in the syringe back into the second end of the tubing in order to transfer the liquids held in the first end of the tubing to the mixing device; and,
(vi) a fluid connection between said mixing device and the reactor inlet port.

28. A method for treating a liquid sample containing organic material utilizing a liquid sample treatment apparatus, the method comprising the steps of:
(a) providing a liquid sample treatment apparatus comprising the following features:
(i) a reactor having reactor inlet and reactor outlet ports and a reactor interior for containing a liquid sample under above-ambient temperature and pressure conditions;
(ii) high-pressure fluid reactor valve members at said reactor inlet and reactor outlet ports, said reactor valve members allowing fluid flow respectively into or out of the reactor interior when in an open-valve mode or, alternatively, capable of sealing the reactor interior when in a closed-valve mode;

(iii) a reactor heating system that is able to rapidly and cyclically heat the reactor interior and a liquid sample sealed in the reactor interior to a temperature of about 150° C. to 650° C. or higher, while the reactor interior and the reactor valve members maintain the sample under sealed conditions; and, (iv) a reactor cooling system adapted for rapidly and cyclically cooling the reactor interior and a reactor product sealed in the reactor interior following a heating cycle;

(b) mixing a known volume of the sample with one or more other liquids selected from oxidizer, acid and dilution water to form a sample mixture;

(c) flowing at least a portion of the sample mixture into the interior of the reactor, said reactor being adapted to be alternately and repeatedly opened and sealed at the reactor inlet and reactor outlet ports;

(d) sealing the portion of sample mixture in the interior of the reactor by closing the valve members at the reactor inlet and reactor outlet ports;

(e) rapidly heating the interior of the reactor and the sample mixture portion inside to a temperature between about 150° C. to about 650° C. for a time sufficient substantially to oxidize the organic material and form the a reactor product;

(f) stopping the heating step and then rapidly cooling the interior of the reactor and the reactor product inside to substantially ambient conditions to form cooled liquid and gaseous reactor products; and, (g) opening the reactor and removing the cooled liquid and gaseous reactor products from the reactor interior.

29. The method of claim 28 further comprising the steps of: (A) prior to the reactor step, sequentially: drawing a known volume of sample into a sample handling system; adding suitable volumes of one or more chemical reagents relative to the volume of sample; mixing the sample and chemical reagents to form a substantially homogeneous sample mixture; and flowing at least a portion of the sample mixture to the reactor interior; and, (B) following the reactor step, sequentially: opening the reactor; using a stream of carrier gas, transferring liquid and gaseous reactor products from the reactor to a gas/liquid separator; separating liquid reactor product from gaseous reactor product; flowing the gaseous reactor product to a chemical detector; and measuring a chemical component in the gaseous reactor product using the chemical detector.

30. The method of claim 29 wherein the chemical reagents are selected from acid and oxidizer.

31. The method of claim 29 further including the step of adding dilution water to the sample and chemical reagents.

32. The method of claim 29 further comprising the steps of mixing the sample and chemical reagents and sparging the solution/suspension with a sparge gas.

33. The method of claim 32 further comprising the step of monitoring the progress of the sparging step by flowing the sparge gas from the mixing/sparging step to the chemical detector for analysis.

34. The method of claim 29 wherein the sample is heated in the reactor to a temperature high enough substantially to oxidize the organic material.

35. The method of claim 29 wherein the sample is heated in the reactor to supercritical fluid temperature/pressure conditions.

36. The method of claim 29 wherein the chemical detector is specific to a material selected from carbon, nitrogen and sulfur oxidation products.

37. The method of claim 29 wherein the chemical detector is a $CO_2$ detector.

38. The method of claim 29 wherein the chemical detector is a non-dispersive infrared (NDIR) detector.

39. The method of claim 38 wherein the NDIR includes an optical filter selective to the wavelength of IR radiation absorbed by the chemical component to be measured.

40. The method of claim 39 wherein the optical filter is selective to $CO_2$.

41. The method of claim of 29 further wherein an AC signal processing element is used for noise rejection/filtering and signal amplitude measurements.

42. The method of claim 29 further wherein the analysis is automated by an electronic/computer automation control system.

43. The method of claim 29 further comprising the step of determining a concentration of a chemical component in the sample using a mathematical formula to correlate a response of the chemical detector to the gaseous reactor product with the concentration of the chemical component.

44. The method of claim 28 further comprising the steps of:
(a) introducing a liquid sample containing particulate material into a mixing chamber having a liquid inlet and outlet, a gas inlet and outlet, and containing a magnetically activated stirring member;
(b) activating the stirring member to move inside the mixing chamber and to agitate the liquid contents and form a sample mixture;
(c) if the removal of gases from the sample mixture is desired, introducing a substantially $CO_2$-free sparge gas to a lower portion of the mixing chamber simultaneously with activation of the stirring member; and,
(d) flowing at least a portion of the sample mixture to the reactor interior.

45. The method of claim 28 further comprising the steps of:
(a) providing a non-dispersive infrared (NDIR) detector apparatus downstream of the reactor to detect a chemical component, said detector apparatus comprising:
   (i) a sealed IR source chamber comprising an IR source chamber purge gas inlet and a purge gas outlet, and containing an infrared radiation source;
   (ii) a sealed IR detector chamber comprising an IR detector chamber purge gas inlet and a purge gas outlet, and containing an infrared detector; and,
   (iii) between the IR source chamber and the IR detector chamber, a sealed optical path chamber having an optical chamber fluid inlet port at a first end of the optical path chamber and an optical chamber fluid outlet port at a second end of the optical path chamber;
(b) flowing a fluid stream containing at least a portion of the reactor product into the optical chamber inlet port, through the optical chamber, and out through the optical chamber outlet port, while IR radiation is being directed through the optical chamber;
(c) throughout step (b), flowing a purge gas that is substantially free of the chemical component being measured through the IR source chamber and the IR detector chamber;
(d) modulating the intensity of the IR radiation directed through the optical chamber; and,
(e) based on the detection response of the detector to the passage of the fluid stream through the optical chamber, calculating a concentration of the chemical component using a mathematical correlation formula.

46. The method of claim 28 further comprising the steps of:
(a) providing a sample/reagent handling system upstream of the reactor, said handling system comprising:
   (i) separate sources of one or more liquids selected from an aqueous solution/suspension, dilution water, and one or more reagents;
   (ii) conduit connections between the sources of the liquid solution/suspension and the reagents and a first end of a length of holding tubing, and a dilution water conduit connection between the dilution water source and a second end of the tubing;
   (iii) a calibrated syringe in fluid communication with the dilution water conduit connection, the syringe having an internal volume that is less than or equal to the internal volume of the tubing; and,
   (iv) fluid valves along each of the conduit connections;
(b) filling the holding tubing with dilution water;
(a) drawing a first measured volume of a first one of the liquid sample or the other liquids into the first end of the tubing by opening and/or closing the appropriate fluid valves and then opening the syringe to draw the first measured volume of dilution water into the syringe from the second end of the tubing;
(d) drawing a second measured volume of a second one of the liquid sample or the other liquids into the first end of the tubing by opening and/or closing the appropriate fluid valves and then additionally opening the syringe to draw the second measured volume of dilution water into the syringe from the second end of the tubing;
(e) transferring the first measured volume of the first one of the liquids and the second measured volume of the second one of the liquids to a mixing location by opening and/or closing the appropriate fluid valves and then closing the syringe to fully discharge all of the dilution water in the syringe back into the second end of the tubing thereby driving the liquids in the first end of the tubing out of the tubing;
(f) mixing the liquids at the mixing location to form a sample mixture; and,
(g) flowing at least a portion of the sample mixture into the reactor interior.

47. The apparatus of claim 27 further characterized by one or more of the following features:
a reactor heating system that is able to heat the reactor interior and a liquid sample sealed in the reactor interior to temperature and pressure high enough to generate supercritical fluid conditions inside the reactor interior, while the reactor interior and the reactor valve members maintain the sample under sealed conditions;
reactor valve members each comprising a valve housing having a main fluid inlet and a main fluid outlet, a moveable valve plunger element inside the valve housing, a front portion of the valve plunger element comprising a polymeric or elastic plunger seal member having a section sized and shaped to mate with and plug the main fluid outlet when the valve plunger element is in advanced position, and to unseal the main fluid outlet when the valve plunger element is in a retracted position;
valve members each comprising a motor for alternately advancing or retracting a valve plunger element;
valve housings each comprising a purge gas inlet and a purge gas outlet whereby a purge gas can be flowed through an interior of a valve housing while a valve plunger element is sealing a main fluid outlet;
a reactor heating system comprising a hollow tubular heating element with the reactor located in the hollow interior of the heating element;
a reactor cooling system comprising a fan located proximate to the reactor and oriented to blow ambient air along an exterior surface of the reactor; and,
a tubular heating element that is open at each end, and further including an associated reactor cooling system that comprises a fan located proximate to one open end of the heating element and is oriented to blow ambient air through the hollow interior of the heating element and along an exterior surface of the reactor.

48. The apparatus of claim 27 further characterized by one or more of the following features:
the combination of a liquid sample inlet; a fluid transport system for drawing a known volume of a liquid sample into the apparatus and for transporting liquids and gases to and through the components of the apparatus including the reactor which is located downstream of the liquid sample inlet; a source of gas and a gas flow control system in communication with a fluid transport system; and, a chemical detector downstream of the reactor to measure a chemical component of the reactor product;
a fluid pumping system in communication with a fluid transport system;
one or more inlets selected from an acid reagent inlet, an oxidizer reagent inlet and a dilution water inlet;
a mixing/sparging chamber upstream from the reactor where a combination of a liquid sample and one or more other liquids can be either mixed or mixed and simultaneously sparged with sparge gas;
a chemical detector for detecting carbon, nitrogen or sulfur oxidation products downstream of the reactor;
a non-dispersive infrared (NDIR) chemical detector downstream of the reactor;
an NDIR downstream of the reactor that includes an optical filter that selectively passes infrared radiation at a wavelength that is absorbed by a chemical component to be measured;
an NDIR downstream of the reactor with an optical filter that selectively passes infrared radiation at a wavelength that is absorbed by carbon oxidation products;
an NDIR downstream of the reactor with an optical filter that selectively passes infrared radiation at a wavelength that is absorbed by $CO_2$;
a gas/liquid separator between the reactor and an NDIR detector downstream of the reactor to remove liquid from the reactor product;
an AC signal processing element effective for noise rejection/filtering and signal amplitude measurements; and,
an electronic/computer automated control system.

49. The apparatus of claim 27 further comprising the following elements:
(A) a sample handling system upstream of the reactor including: multiple valves and a syringe connected through a three-way valve to both a coil of tubing and a reservoir containing low-TOC dilution water, wherein the volume of the coil is at least a large as the volume of the syringe; a pump component effective to draw sample from a sample source and deliver it by a conduit connection to a fluid interconnection element; a mixing/sparging chamber connected to the coil of tubing, said chamber including a sparging element for sparging $CO_2$-free gas through a solution/suspension in the chamber; a source of compressed $CO_2$-free gas connected to the sparging element and a gas control module to control the flow and pressure of such gas; and a pump component and associated conduit to transfer at least a portion of the solution/suspension from the mixing/sparging chamber to the reactor; (B) a source of carrier gas connected to the reactor; and (C) a reactor product handling system downstream of the reactor including a conduit carrying the reactor product sequentially through a gas/liquid separator, an inline filter, and then to a $CO_2$ detector; and an associated automated control system comprising electrical connections and operational software adapted to operate fluid valves and other system control elements according to a predetermined sequence and/or timing or, alternatively, in accordance with feedback received from various system monitors.

50. The apparatus of claim 27 further comprising a mixing system upstream of the reactor for mixing a liquid sample containing particulate material with one or more other liquid components, said mixing system comprising:
   (A) a sealed tubular mixing container having a liquid inlet/gas outlet section at a first container end, said liquid inlet/gas outlet section including a sample inlet and a sparge gas outlet; a liquid outlet/gas inlet section at a second container end, said liquid outlet/gas inlet section including a sparge gas inlet and a sample outlet; and, between said liquid inlet/gas outlet section and said liquid outlet/gas inlet section, a fluid mixing region;
   (B) a magnetically activatable stirrer element inside said fluid mixing region;
   (C) an annular solenoid coil surrounding at least a portion of said fluid mixing region, said solenoid coil being activatable by a series of electric current pulses to move the stirrer element inside the fluid mixing region; and,
   (D) a porous gas disperser located between the sparge gas inlet and the fluid mixing region.

51. The apparatus of claim 27 wherein each of the reactor valve members includes a purgeable fluid sealing valve assembly comprising:
   (A) a valve housing having a main fluid inlet and a main fluid outlet;
   (B) a moveable plunger element inside the valve housing, a front portion of the valve plunger element comprising a plunger seal member sized and shaped to be seated on and plug the main fluid outlet when the valve plunger element is in an advanced position, and to unseal the main fluid outlet when the plunger is in a retracted position; and,
   (C) the valve housing further comprising a valve purge gas inlet and a valve purge gas outlet whereby a purge gas can be flowed through the interior of the valve housing while the valve plunger element is sealing the main fluid outlet.

52. The apparatus of claim 27 further comprising a purgeable non-dispersive infrared (NDIR) detector downstream of said reactor and in fluid communication with the reactor outlet port, said detector comprising:
   (A) an IR source chamber comprising an IR source chamber purge gas inlet and a purge gas outlet, and containing an infrared radiation source;
   (B) an IR detector chamber comprising an IR detector chamber purge gas inlet and a purge gas outlet, and containing an infrared detector; and,
   (C) between the IR source chamber and the IR detector chamber, an optical path chamber having an optical chamber gas inlet port at a first end of the optical path chamber and an optical chamber gas outlet port at a second end of the optical path chamber.

53. The method of claim 28 further characterized by one or more of the following additional steps:
   the additional steps of: (A) prior to the reactor step, sequentially: drawing a known volume of sample into a sample handling system; adding suitable volumes of one or more chemical reagents relative to the volume of sample; mixing the sample and chemical reagents to form a substantially homogeneous sample mixture; and flowing at least a portion of the sample mixture to the reactor interior; and, (B) following the reactor step, sequentially: opening the reactor; using a stream of carrier gas, transferring liquid and gaseous reactor products from the reactor to a gas/liquid separator; separating liquid reactor product from gaseous reactor product; flowing the gaseous reactor product to a chemical detector; and measuring a chemical component in the gaseous reactor product using a chemical detector;
   the additional steps of mixing the sample and chemical reagents and sparging the solution/suspension with a sparge gas;
   the additional step of: monitoring the progress of a mixing/sparging step by flowing sparge gas from the mixing/sparging step to a chemical detector for analysis;
   the additional step of: measuring a chemical component in the gaseous reactor product using a chemical detector selective to a material selected from carbon, nitrogen and sulfur oxidation products;
   the additional step of: measuring a chemical component in the gaseous reactor product using a $CO_2$ detector;
   the additional step of: measuring a chemical component in the gaseous reactor product using a non-dispersive infrared (NDIR) detector:
   the additional step of measuring a chemical component in the gaseous reactor product using an NDIR detector that includes an optical filter that selectively passes infrared radiation at a wavelength that is absorbed by a chemical component to be measured;
   the additional step of: measuring a chemical component in the gaseous reactor product using an NDIR detector that includes an optical filter that selectively passes infrared radiation at a wavelength that is absorbed by $CO_2$;
   the additional step of: using an AC signal processing element for noise rejection filtering and signal amplitude measurements;
   the additional step of: automating the analysis using an electronic/computer automation control system; and,
   the additional step of: determining a concentration of a chemical component in the sample using a mathematical formula to correlate a response of a chemical detector to a gaseous reactor product with the concentration of the chemical component.

54. The method of claim 28 further comprising the steps of:
   (A) introducing a liquid sample containing particular material into a mixing chamber having a liquid inlet and outlet, a gas inlet and outlet, and containing a magnetically activated stirring member;
   (B) activating the stirring member to move inside the mixing chamber and to agitate the liquid contents and form a sample mixture;
   (C) introducing a substantially $CO_2$-free sparge gas to a lower portion of the mixing chamber simultaneously with activation of the stirring member; and,
   (D) flowing at least a portion of the sample mixture from the mixing chamber to the reactor interior.

55. The method of claim 28 further comprising the steps of:
   (A) providing a non-dispersive infrared (NDIR) detector apparatus downstream of the reactor to detect a chemical component, said detector apparatus comprising:
      (i) a sealed IR source chamber comprising an IR source chamber purge gas inlet and a purge gas outlet, and containing an infrared radiation source;

(ii) a sealed IR detector chamber comprising an IR detector chamber purge gas inlet and a purge gas outlet, and containing an infrared detector; and, (iii) between the IR source chamber and the IR detector chamber, a sealed optical path chamber having an optical chamber fluid inlet port at a first end of the optical path chamber and an optical chamber fluid outlet port at a second end of the optical path chamber;

(B) flowing a fluid stream containing at least a portion of the reactor product into the optical chamber inlet port, through the optical chamber, and out through the optical chamber outlet port, while IR radiation is being directed through the optical chamber;

(C) throughout step (B), flowing a purge gas that is substantially free of the chemical component being measured through the IR source chamber and the IR detector chamber;

(D) modulating the intensity of the IR radiation directed through the optical chamber; and, (E) based on the detection response of the detector to the passage of the fluid stream through the optical chamber, calculating a concentration of the chemical component using a mathematical correlation formula.

56. The method of claim 28 further comprising the steps of:

(A) providing a sample/reagent handling system upstream of the reactor, said handling system comprising:

(i) separate sources of one or more liquids selected from an aqueous solution/suspension, dilution water, and one or more reagents;

(ii) conduit connections between the sources of the liquid solution/suspension and the reagents and a first end of a length of holding tubing, and a dilution water conduit connection between the dilution water source and a second end of the tubing;

(iii) a calibrated syringe in fluid communication with the dilution water conduit connection, the syringe having an internal volume that is less than or equal to the internal volume of the tubing; and, (iv) fluid valves along each of the conduit connections;

(B) filling the holding tubing with dilution water;

(C) drawing a first measured volume of a first one of the liquid sample or the other liquids into the first end of the tubing by opening and/or closing the appropriate fluid valves and then opening the syringe to draw the first measured volume of dilution water into the syringe from the second end of the tubing;

(D) drawing a second measured volume of a second one of the liquid sample or the other liquids into the first end of the tubing by opening and/or closing the appropriate fluid valves and then additionally opening the syringe to draw the second measured volume of dilution water into the syringe from the second end of the tubing;

(E) transferring the first measured volume of the first one of the liquids and the second measured volume of the second one of the liquids to a mixing location by opening and/or closing the appropriate fluid valves and then closing the syringe to fully discharge all of the dilution water in the syringe back into the second end of the tubing thereby driving the liquids in the first end of the tubing out of the tubing;

(F) mixing the liquids at the mixing location to form a sample mixture; and, (G) flowing at least a portion of the sample mixture from the mixing location into the reactor interior.

* * * * *